United States Patent
Kim

(10) Patent No.: US 11,026,655 B2
(45) Date of Patent: Jun. 8, 2021

(54) ULTRASOUND DIAGNOSTIC APPARATUS AND METHOD OF GENERATING B-FLOW ULTRASOUND IMAGE WITH SINGLE TRANSMISSION AND RECEPTION EVENT

(71) Applicant: SAMSUNG ELECTRONICS CO., LTD., Suwon-si (KR)

(72) Inventor: Kang-Sik Kim, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1183 days.

(21) Appl. No.: 14/667,053

(22) Filed: Mar. 24, 2015

(65) Prior Publication Data

US 2016/0089108 A1 Mar. 31, 2016

(30) Foreign Application Priority Data

Sep. 26, 2014 (KR) .......................... 10-2014-0129116
Oct. 14, 2014 (KR) .......................... 10-2014-0138617

(51) Int. Cl.
*A61B 8/06* (2006.01)
*G01S 7/52* (2006.01)
(Continued)

(52) U.S. Cl.
CPC .............. *A61B 8/06* (2013.01); *A61B 8/4472* (2013.01); *A61B 8/5207* (2013.01);
(Continued)

(58) Field of Classification Search
CPC ............. G01S 7/52085; G01S 7/52066; G01S 15/8979; G01S 7/003; A61B 8/06;
(Continued)

(56) References Cited

U.S. PATENT DOCUMENTS 5,940,123 A * 8/1999 Daigle ................ G01S 7/52044
348/163
6,210,332 B1 * 4/2001 Chiao ................. G01S 15/8988
600/443

(Continued)

FOREIGN PATENT DOCUMENTS

JP 2004129967 A 4/2004
KR 1020080034660 A 4/2008

(Continued)

OTHER PUBLICATIONS

Montaldo et al,; Coherent plane-wave compounding for very high frame rate ultrasonography and transient elastography; IEEE vol. 56, Issue: 3, Mar. 2009 (Year: 2009).*

(Continued)

*Primary Examiner* — Serkan Akar

(74) *Attorney, Agent, or Firm* — Sughrue Mion, PLLC

(57) ABSTRACT

An ultrasound image is generated by repeatedly transmitting an ultrasound signal to scan lines in an object and receiving echo signals respectively corresponding to the scan lines. Each of at least three echo signal groups is formed to include the echo signals received as a result of a single execution of transmitting the ultrasound signal and receiving corresponding echo signals. A B-flow image is generated by partially overlapping the echo signal groups and represents a tissue component and a blood flow component.

17 Claims, 31 Drawing Sheets

(51) Int. Cl.
*A61B 8/08* (2006.01)
*A61B 8/14* (2006.01)
*A61B 8/00* (2006.01)
*G01S 15/89* (2006.01)
*G01S 7/00* (2006.01)

(52) U.S. Cl.
CPC ...... *G01S 7/52066* (2013.01); *G01S 7/52085* (2013.01); *G01S 15/8979* (2013.01); *A61B 8/14* (2013.01); *A61B 8/4427* (2013.01); *A61B 8/463* (2013.01); *A61B 8/565* (2013.01); *G01S 7/003* (2013.01)

(58) Field of Classification Search
CPC ... A61B 8/4472; A61B 8/5207; A61B 8/4427; A61B 8/565; A61B 8/14; A61B 8/463
See application file for complete search history.

(56) References Cited

U.S. PATENT DOCUMENTS

| | | | | |
|---|---|---|---|---|
| 6,406,430 | B1* | 6/2002 | Ishrak | G01S 7/52039 600/441 |
| 6,589,177 | B1 | 7/2003 | Detmer et al. | |
| 6,685,645 | B1* | 2/2004 | McLaughlin | A61B 8/08 600/447 |
| 2003/0216644 | A1* | 11/2003 | Hall | A61B 8/06 600/437 |
| 2008/0086054 | A1 | 4/2008 | Slayton et al. | |
| 2009/0036772 | A1* | 2/2009 | Lu | G01S 7/52046 600/437 |
| 2009/0069692 | A1* | 3/2009 | Cooley | G01S 7/52028 600/459 |
| 2009/0069693 | A1* | 3/2009 | Burcher | G01S 7/52028 600/459 |
| 2009/0326379 | A1* | 12/2009 | Daigle | A61B 8/06 600/453 |
| 2012/0130248 | A1* | 5/2012 | Fatemi | A61B 8/06 600/454 |
| 2012/0215110 | A1* | 8/2012 | Wilkening | A61B 8/488 600/453 |
| 2014/0018680 | A1* | 1/2014 | Guracar | A61B 8/463 600/440 |
| 2014/0371594 | A1* | 12/2014 | Flynn | A61B 8/488 600/454 |
| 2015/0297183 | A1* | 10/2015 | Freeman | G01S 15/8927 600/459 |
| 2016/0132187 | A1* | 5/2016 | Lu | G01S 7/5208 345/177 |

FOREIGN PATENT DOCUMENTS

KR 100978482 B1 8/2010
KR 10-2013-0115822 A 10/2013

OTHER PUBLICATIONS

Communication dated Sep. 17, 2015, issued by the International Searching Authority in counterpart International Application No. PCT/KR2015/006056.
Communication dated May 11, 2018 by the European Patent Office in counterpart European Patent Application No. 15843149.4.

* cited by examiner

ULTRASOUND DIAGNOSTIC APPARATUS AND METHOD OF GENERATING B-FLOW ULTRASOUND IMAGE WITH SINGLE TRANSMISSION AND RECEPTION EVENT

CROSS-REFERENCE TO RELATED APPLICATIONS

This application claims priority from Korean Patent Application No. 10-2014-0129116, filed on Sep. 26, 2014, and Korean Patent Application No. 10-2014-0138617, filed on Oct. 14, 2014, in the Korean Intellectual Property Office, the disclosures of which are incorporated herein in their entireties by reference.

BACKGROUND

1. Field

One or more exemplary embodiments relate to an ultrasound diagnostic apparatus and a method of generating an ultrasound image.

2. Description of the Related Art

An ultrasound diagnostic apparatus transmits ultrasound signals generated by a probe to an object and receives echo signals reflected from the object, thereby obtaining images of the internal areas of the object. In particular, an ultrasound diagnostic apparatus may be used for various medical purposes such as observation of the internal areas of an object, detection of foreign substances, and assessment of injuries. An ultrasound diagnostic apparatus may display information regarding an object in real-time. Furthermore, there is no risk of radioactive exposure using an ultrasound diagnostic apparatus, unlike in the X-ray, and, thus, the ultrasound diagnostic apparatus is safe and widely used.

SUMMARY

According to an aspect of an exemplary embodiment, a method of generating an ultrasound image includes: transmitting an ultrasound signal to scan lines in an object; receiving echo signals respectively corresponding to the scan lines from the object, the echo signals forming echo signal groups; and generating a B-flow image by partially overlapping the echo signal groups that are acquired by repeatedly performing the transmitting of the ultrasound signal and the receiving the echo signals, wherein a single echo signal group includes the echo signals received from the scan lines in response to a respective transmission signal, and the B-flow image represents a tissue component and a blood flow component.

The transmitting of the ultrasound signal may include transmitting an ultrasonic plane wave.

The transmitting of the ultrasound signal may include transmitting a tilted ultrasonic plane wave.

The transmitting of the ultrasound signal may include transmitting the ultrasound signal that is focused on a focal point outside the B-flow image within the object.

The transmitting of the ultrasound signal may include transmitting the ultrasound signal that is focused on a focal point outside the object.

The generating of the B-flow image may include: generating a first frame by using N echo signal groups; and generating a second frame by using some of the N echo signal groups and M echo signal groups acquired after obtaining the N echo signal groups where N is a natural number greater than or equal to 2, and M is a natural number less than N.

A number of the N echo signal groups may be equal to a number of ensembles corresponding to a number of transmission/reception operations for acquiring a single frame.

The generating of the second frame may include generating the second frame by using N–M echo signal groups selected from the N echo signal groups and the M echo signal groups.

The generating of the B-flow image may include: generating a first frame by using first through Nth echo signal groups that are sequentially acquired; and generating a second frame by using Nth–M through Nth+M echo signal groups that are sequentially acquired where N is a natural number greater than or equal to 2, and M is a natural number less than N.

The generating of the B-flow image may include: extracting B-flow data from the echo signals; and generating frames that constitute the B-flow image by using the extracted B-flow data.

The generating of the B-flow image may further include performing decoding filtering on the B-flow data extracted from the echo signals for each scan line, each of the echo signals being included in each of the echo signal groups.

The decoding filtering may be performed by applying a weighted sum to the echo signals for each scan line, to attenuate a signal corresponding to the tissue component and increase a signal corresponding to the blood flow component, among the echo signals.

The generating of the plurality of frames may include: generating a scan line image for each scan line based on a result of the decoding filtering; generating a frame from scan line images corresponding to the scan lines, respectively; and generating the B-flow image including the frames that are sequentially acquired by repeatedly performing the generating the scan line image and the generating the frame.

The generating of the B-flow image may further include performing color mapping on the extracted B-flow data, wherein the generating of the frames may include generating a color image.

The method may further include extracting B-mode data from the echo signals and generating a B-mode image by using the extracted B-mode data.

The method may further include displaying the B-flow image and the B-mode image.

The transmitting of the ultrasound signal may include transmitting an ultrasonic plane wave to a region corresponding to a plurality of transducers by applying a same delay time for the plurality of transducers.

The transmitting of the ultrasound signal may include transmitting an ultrasonic plane wave to a region corresponding to some of a plurality of transducers, which are arranged adjacent to one another, by applying a same delay time for the some of the plurality of transducers which are adjacently arranged.

According to an aspect of an exemplary embodiment, an ultrasound diagnostic apparatus includes: a transceiver including a transmitter configured to transmit an ultrasound signal to scan lines in an object and a receiver configured to receive echo signals respectively corresponding to the scan lines from the object, the echo signals forming echo signal groups; and an image processor configured to generate a B-flow image by partially overlapping the echo signal groups that are acquired by repeatedly transmitting the ultrasound signal and receiving the echo signals, wherein a single echo signal group includes the echo signals received from the scan lines in response to a respective transmission signal, and the B-flow image represents a tissue component and a blood flow component.

The transmitter may transmit the ultrasound signal as an ultrasonic plane wave, to the object.

The transmitter may transmit the ultrasound signal as a tilted ultrasonic plane wave, to the object.

The transmitter may transmit to the object the ultrasound signal that is focused on a focal point outside the B-flow image within the object.

The transmitter may transmit to the object the ultrasound signal that is focused on a focal point outside the object.

The image processor may generate a first frame by using N echo signal groups and a second frame by using some of the N echo signal groups and M echo signal groups acquired after obtaining the N echo signal groups, where N is a natural number greater than or equal to 2, and M is a natural number less than N.

A number of the N echo signal groups may be equal to a number of ensembles corresponding to a number of transmission/reception operations for acquiring a single frame.

The image processor may generate the second frame by using N–M echo signal groups selected among the N echo signal groups and the M echo signal groups.

The image processor may generate a first frame by using first through Nth echo signal groups that are sequentially acquired and a second frame by using Nth–M through Nth+M echo signal groups that are sequentially acquired, wherein N is a natural number greater than or equal to 2, and M is a natural number less than N.

The image generator may include: a B-flow data extractor for extracting B-flow data from the echo signals; and an image generator for generating frames that constitute the B-flow image by using the extracted B-flow data.

The image processor may further include a decoding filter for performing decoding filtering on the B-flow data extracted from the echo signals for each scan line, each of the echo signals being included in each of the echo signal groups.

The decoding filter may perform the decoding filtering by applying a weighted sum to the echo signals for each scan line, to attenuate a signal corresponding to the tissue component and increase a signal corresponding to the blood flow component, among the echo signals.

The image processor may generate a scan line image for each scan line based on a result of the decoding filtering, generate a frame from scan line images corresponding to the scan lines, respectively, and generate the B-flow image including frames that are sequentially acquired by repeatedly performing generating of the scan line image and generating of the frame.

The image processor may further include a color mapper for performing color mapping on the extracted B-flow data, wherein the image generator generates the frames as a color image.

The image processor may further include a B-mode image generator that extracts B-mode data from the echo signals and generates a B-mode image by using the extracted B-mode data.

The apparatus may further include a display for displaying the B-flow image and the B-mode image.

The transmitter may transmit the ultrasound signal as an ultrasonic plane wave to a region corresponding to a plurality of transducers by applying a same delay time for the plurality of transducers.

The transmitter may transmit the ultrasound signal as an ultrasonic plane wave to a region corresponding to some of a plurality of transducers, which are arranged adjacent to one another, by applying a same delay time for the some of the plurality of transducers which are adjacently arranged.

According to an aspect of an exemplary embodiment, a non-transitory computer-readable recording medium has recorded thereon a program for executing a method of generating an ultrasound image, wherein the method includes: transmitting an ultrasound signal to scan lines in an object; receiving echo signals respectively corresponding to the scan lines from the object, the echo signals forming echo signal groups; and generating a B-flow image by partially overlapping the echo signal groups that are acquired by repeatedly performing the transmitting the ultrasound signal and the receiving the echo signals, wherein a single echo signal group includes the echo signals received from the scan lines in response to a respective transmission signal, and the B-flow image represents a tissue component and a blood flow component.

BRIEF DESCRIPTION OF THE DRAWINGS

The above and/or other aspects will become more apparent by describing certain exemplary embodiments, with reference to the accompanying drawings, in which.

DETAILED DESCRIPTION

Figure 1:
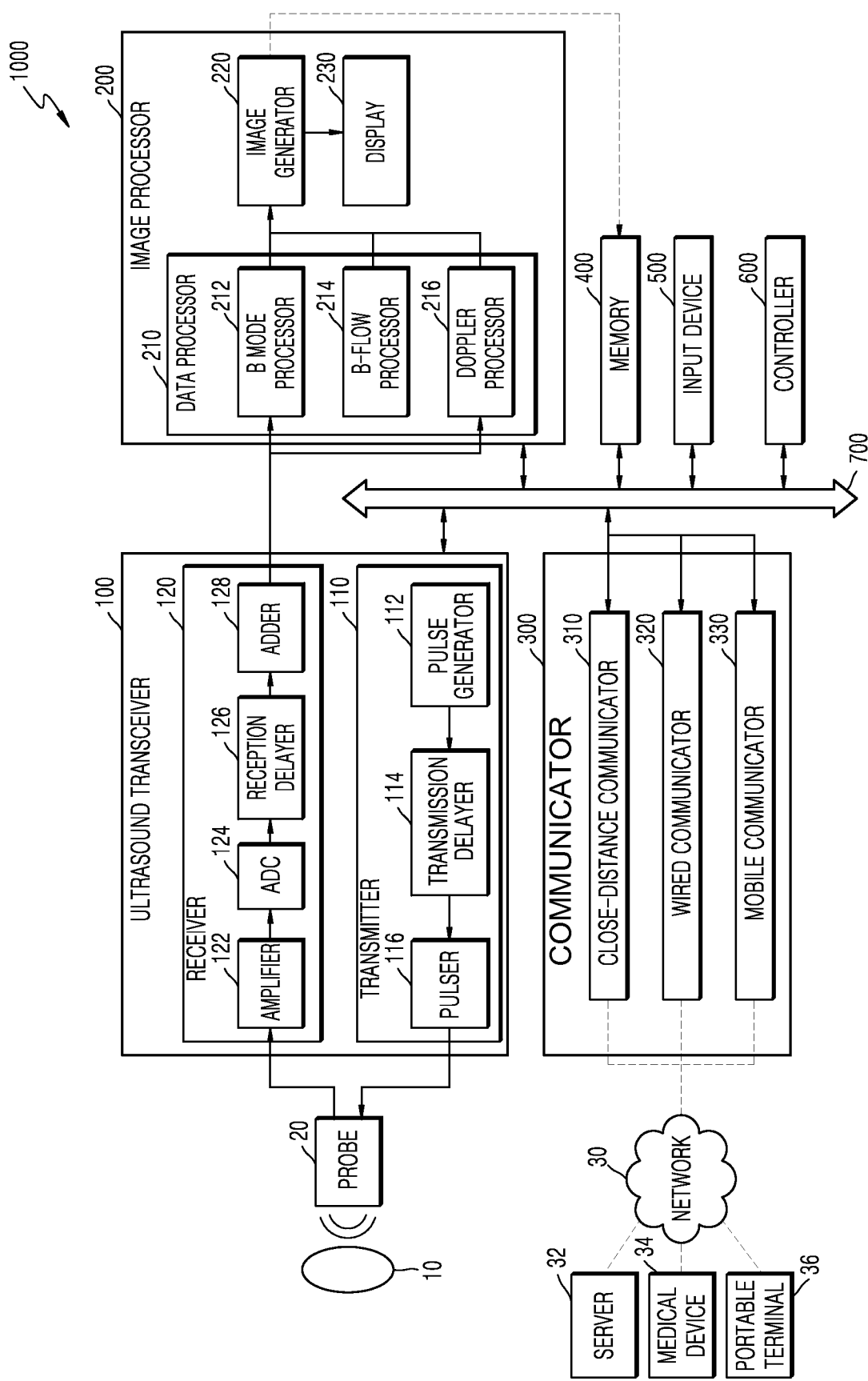
FIG. 1 is a block diagram of a configuration of an ultrasound diagnostic apparatus according to an exemplary embodiment.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Expressions such as "at least one of," when preceding a list of elements, modify the entire list of elements and do not modify the individual elements of the list.

Throughout the specification, when a component "includes" or "comprises" an element, unless there is a particular description contrary thereto, it should be understood that the component can further include other elements, not excluding the other elements. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object obtained using an ultrasound wave. Furthermore, in the present specification, an "object" may include a person or an animal, or a part of a person or an animal. For example, the object may include organs such as the liver, the heart, the womb, the brain, a breast, and the abdomen, or a blood vessel. Furthermore, the "object" may include a phantom. The phantom is a material having a volume that is approximately close to the density and effective atomic number of a living organism.

In the present specification, a "user" refers to a medical professional, such as a doctor, a nurse, a medical laboratory technologist, and a medical imaging expert, and a technician who repairs a medical apparatus, but not limited thereto.

FIG. 1 is a block diagram of a configuration of an ultrasound diagnostic apparatus 1000 according to an exemplary embodiment.

Referring to FIG. 1, the ultrasound diagnostic apparatus 1000 includes a probe or probes 20, an ultrasound transceiver 100, an image processor 200, a communicator 300, a memory 400, an input device 500, and a controller 600, and the components may be connected to one another via buses 700.

The ultrasound diagnostic apparatus 1000 may be a cart type device or a portable device. Examples of portable ultrasound diagnostic apparatuses may include a Picture Archiving and Communications System (PACS) viewer, a smartphone, a laptop computer, a personal digital assistant (PDA), and a tablet personal computer (PC). However, exemplary embodiments are not limited thereto.

The probe 20 transmits ultrasound signals to an object 10, based on a driving signal applied by the ultrasound transceiver 100, and receives echo signals reflected from the object 10. The probe 20 includes a plurality of transducers that oscillate in response to electric signals transmitted thereto and generate acoustic energy, i.e., ultrasound waves. The probe 20 may be connected to a main body of the ultrasound diagnostic apparatus 1000 by wire or wirelessly.

A transmitter 110 supplies a driving signal to the probe 20 and includes a pulse generator 112, a transmission delayer 114, and a pulser 116. The pulse generator 112 generates pulses for forming transmission ultrasound waves based on a predetermined pulse repetition frequency (PRF), and the transmission delayer 114 applies a delay time for determining transmission directionality to the pulses. Pulses, to which a delay time is applied, correspond to a plurality of piezoelectric vibrators included in the probe 20, respectively. The pulser 116 applies a driving signal (or a driving pulse) to the probe 20 at a timing corresponding to each pulse to which a delay time is applied.

A receiver 120 generates ultrasound data by processing echo signals received from the probe 20. The receiver 120 may include an amplifier 122, an analog-to-digital converter (ADC) 124, a reception delayer 126, and an adder 128. The amplifier 122 amplifies echo signals in each channel, and the ADC 124 performs analog-to-digital conversion on the amplified echo signals. The reception delayer 126 applies delay times for determining reception directionality to the analog-to-digital converted echo signals, and the adder 128 generates ultrasound data by summing the echo signals processed by the reception delayer 126. According to exemplary embodiments, the receiver 120 may omit the amplifier 122. For example, if the sensitivity of the probe 20 or the capability of the ADC 124 to process bits is enhanced, the amplifier 122 may be omitted.

The image processor 200 generates an ultrasound image by processing ultrasound data generated by the ultrasound transceiver 100 and displays the ultrasound image. For example, an ultrasound image may include a gray-scale ultrasound image obtained by scanning an object in an amplitude (A) mode, a brightness (B) mode, and/or a motion (M) mode, and a Doppler image representing a moving object by using a Doppler effect. The Doppler image may include a blood flow Doppler image (also called a color Doppler image) showing a flow of blood, a tissue Doppler image showing movement of tissue, and a spectral Doppler image showing the speed at which an object moves as a waveform.

A B-mode processor 212 extracts B-mode components from ultrasound data and processes the B-mode components. An image generator 220 may generate an ultrasound image in which signal intensities are represented as brightness based on the extracted B-mode components.

A B-flow processor 214 extracts B-flow components from ultrasound data. The image generator 220 may generate an ultrasound image including a B-flow image representing a tissue component and a blood flow component of the object 10 based on the B-flow components extracted by the B-flow processor 214

Similarly, a Doppler processor 216 may extract Doppler components from ultrasound data, and the image generator 220 may generate a Doppler image indicating movement of an object as colors or waveforms based on the extracted Doppler components.

In an exemplary embodiment, the image generator 220 may generate a three-dimensional (3D) ultrasound image via volume-rendering of volume data and/or an elasticity image which is a visual representation of the degree of deformation of the object 10 due to pressure. The image generator 220 may display various additional information in an ultrasound image by using text and graphics. The generated ultrasound image may be stored in the memory 400.

A display 230 displays and outputs the generated ultrasound image. The display 230 may also display various information processed by the ultrasound diagnostic apparatus 1000 on a screen via a graphical user interface (GUI). For example, the ultrasound diagnostic apparatus 1000 may include two or more displays according to exemplary embodiments.

The communicator 300 is connected to a network 30 by wire or wirelessly and communicates with an external device or server. The communicator 300 may exchange data with a hospital server or another medical device in a hospital that is connected via a Picture Archiving and Communications System (PACS). The communicator 300 may perform data communication according to the Digital Imaging and Communications in Medicine (DICOM) standard.

The communicator 300 may transmit or receive data related to diagnosis of the object 10, e. g., an ultrasound image, ultrasound data, and Doppler data of the object 10, via the network 30. The communicator 300 may also transmit or receive medical images obtained by other medical apparatuses such as a computed tomography (CT) apparatus, a magnetic resonance imaging (MRI) apparatus, and/or an X-ray apparatus. The communicator 300 may receive information related to a diagnosis history or a treatment schedule of a patient from a server and utilize the information to diagnose the patient, i.e., the object 10. The communicator 300 may perform data communication with a server or a medical device in a hospital as well as a portable terminal of a doctor or a patient.

The communicator 300 is connected to the network 30 in a wired or wireless manner and may exchange data with a server 32, a medical device 34, or a portable terminal 36. The communicator 300 may include at least one component that enables communication with an external device, e.g., a close-distance communicator 310, a wired communicator 320, and/or a mobile communicator 330.

The close-distance communicator 310 is a module for performing close-distance communication with a device that is within a predetermined distance. Examples of close-distance communication technology include a wireless Local Area Network (LAN), Wi-Fi, Bluetooth, ZigBee, Wi-Fi Direct (WFD), Ultra Wideband (UWB), Infrared Data Association (IrDA), Bluetooth Low Energy (BLE), and Near Field Communication (NFC), but this is not limiting.

The wired communicator 320 is a module for performing communication by using an electric signal or an optical signal by using, for example, a paired cable, a coaxial cable, an optical fiber cable, and/or an Ethernet cable.

The mobile communicator 330 transmits or receives wireless signals to or from at least one of a base station, an external terminal, and a server on a mobile communication network. Here, the wireless signals may include voice call signals, video call signals, or various types of data for transmission and reception of text/multimedia messages.

The memory 400 stores various data processed by the ultrasound diagnostic apparatus 1000. For example, the memory 400 may store medical data related to the diagnosis of the object 10, such as ultrasound data and ultrasound images that are input or output, and may also store algorithms or programs that are executed in the ultrasound diagnostic apparatus 1000.

The memory 400 may include various storage media such as a flash memory, a hard disk drive, and Electrically Erasable Programmable Read-Only Memory (EEPROM). The ultrasound diagnostic apparatus 1000 may utilize web storage or a cloud server that functions as the memory 400 online.

The input device 500 is a device via which a user inputs data for controlling the ultrasound diagnostic apparatus 1000. The input device 500 may include hardware components, such as a keypad, a mouse, a touch panel, a touch screen, a trackball, and a jog switch. However, exemplary embodiments are not limited thereto, and the input device 500 may further include various other input elements such as an electrocardiogram measuring module, a respiration measuring module, a voice recognition sensor, a gesture recognition sensor, a fingerprint recognition sensor, an iris recognition sensor, a depth sensor, a distance sensor, etc.

The controller 600 may control operations of the ultrasound diagnostic apparatus 1000. For example, the controller 600 may control operations of the probe 20, the ultrasound transceiver 100, the image processor 200, the communicator 300, the memory 400, and the input device 500.

All or some of the probe 20, the ultrasound transceiver 100, the image processor 200, the communicator 300, the memory 400, the input device 500, and the controller 600 may be operated by software modules. However, exemplary embodiments are not limited thereto, and some of the above components may be operated by hardware modules. Furthermore, at least one of the ultrasound transceiver 100, the image processor 200, and the communicator 300 may be included in the controller 600, but exemplary embodiments are not limited thereto.

The ultrasound diagnostic apparatus according to one or more exemplary embodiments may be included in an ultrasound diagnostic system. Alternatively, the ultrasound diagnostic apparatus may be included in the server 32, the medical device 34, or the portable terminal 36 connected to at least one ultrasound diagnostic system via the network 30. Here, the server 32, the medical device 34, or the portable terminal 36 may be an image processing apparatus capable of displaying, storing, or processing an ultrasound image. For example, the ultrasound diagnostic apparatus according to one or more exemplary embodiment may be in a form of the server 32, the medical device 34, or the portable terminal 36, and may be a picture archiving and communication system (PACS) capable of displaying, storing, or processing an ultrasound image.

Figure 2:
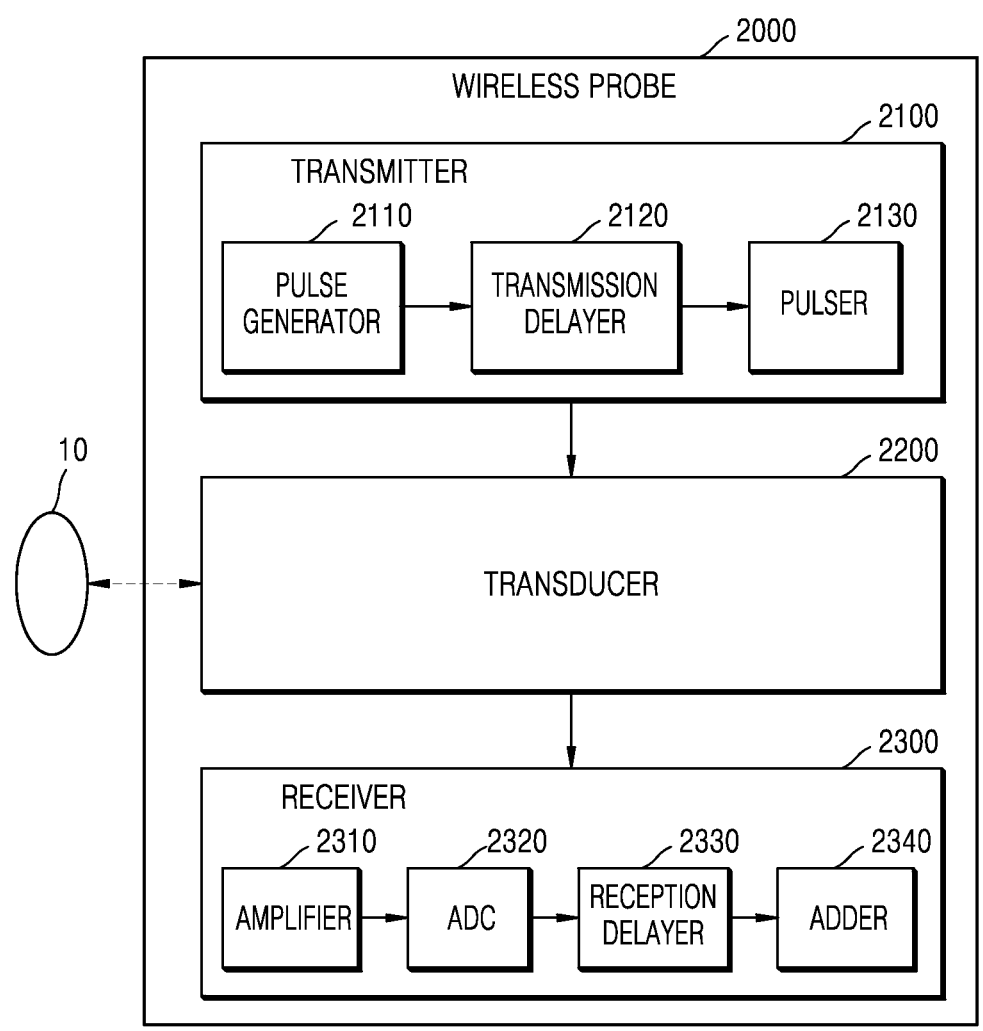
FIG. 2 is a block diagram of a configuration of a wireless probe according to an exemplary embodiment.

FIG. 2 is a block diagram of a configuration of a wireless probe 2000 according to an exemplary embodiment.

Referring to FIG. 2, the wireless probe 2000 includes a plurality of transducers and may include some or all of the components of the ultrasound transceiver 100 according to exemplary embodiments.

The wireless probe 2000 according to the present exemplary embodiment includes a transmitter 2100, a transducer 2200, and a receiver 2300. The same descriptions as already presented with respect to FIG. 1 are omitted. According to exemplary embodiments, the wireless probe 2000 may include a reception delayer 2330 and/or an adder 2340. The wireless probe 2000 may transmit ultrasound signals to an object 10, receive echo signals, generate ultrasound data, and transmit the ultrasound data wirelessly to the ultrasound diagnostic apparatus 1000 of FIG. 1.

Figure 3:
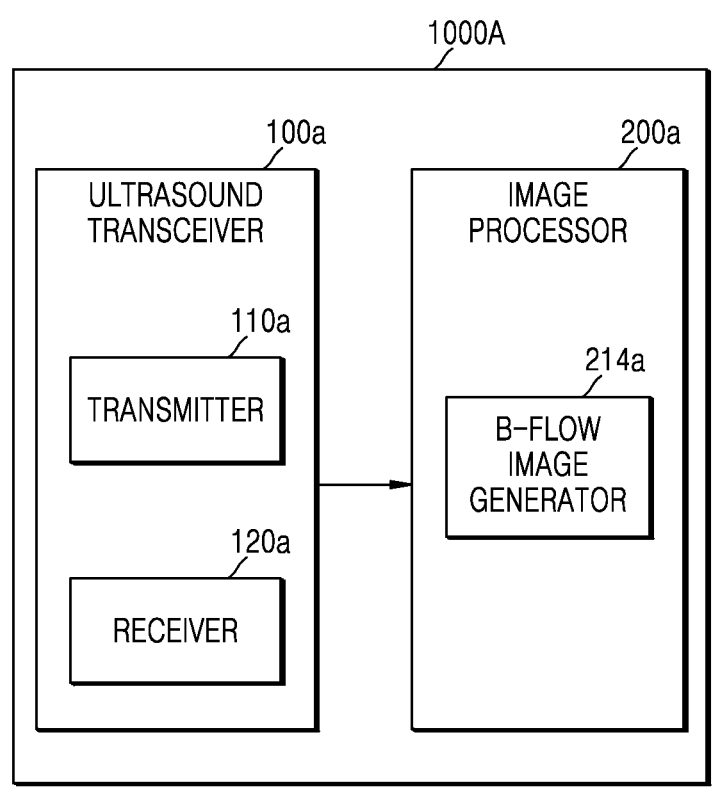
FIG. 3 is a block diagram of a configuration of an ultrasound diagnostic apparatus according to an exemplary embodiment.

FIG. 3 is a block diagram of a configuration of an ultrasound diagnostic apparatus 1000A according to another exemplary embodiment.

Referring to FIG. 3, the ultrasound diagnostic apparatus 1000A according to the present exemplary embodiment may include an ultrasound transceiver 100a and an image processor 200a. The ultrasound transceiver 100a may include a transmitter 110a and a receiver 120a, and the image processor 200a may include a B-flow image generator 214a. Since the ultrasound diagnostic apparatus 1000A is a modified example of the ultrasound diagnostic apparatus 1000 of FIG. 1 the descriptions with respect to the ultrasound diagnostic apparatus 1000 may also be applied to the ultrasound diagnostic apparatus 1000A. Thus, the ultrasound diagnostic apparatus 1000A may further include components shown in FIG. 1 other than the ultrasound transceiver 100a and the image processor 200a, e.g., the display 230, the communicator 300, and the memory 400.

The ultrasound transceiver 100a may transmit or receive ultrasound signals to or from the object 10. The transmitter 110a may transmit ultrasound signals to the object 10. In detail, an ultrasound signal is transmitted simultaneously to a plurality of scan lines in the object 10. The receiver 120a may simultaneously receive a plurality of echo signals corresponding to the plurality scan lines, respectively, from the object 10.

In an exemplary embodiment, the transmitter 110a may transmit an ultrasound signal, i.e., a plane wave, to the object 10. In this case, since the ultrasound signal is transmitted in the form of an unfocused plane wave, the ultrasound signal is not focused on a single point in the object 10. Thus, the ultrasound signal may be transmitted simultaneously to a plurality of scan lines in the object 10. However, exemplary embodiments are not limited thereto, and the ultrasound signal may have various forms to be transmitted simultaneously to the plurality of scan lines in the object 10, and will be described in more detail below with reference to FIGS. 7A through 7D.

The transmitter 110a and the receiver 120a may perform transmission and reception operations repeatedly. For example, the transmitter 110a may sequentially transmit first through Nth ultrasound signals, and the receiver 120a may sequentially receive first through Nth echo signal groups. N is the number of ensembles corresponding to the number of transmission/reception operations for acquiring a single frame and is a natural number greater than or equal to 2. In an exemplary embodiment, the transmitter 110a and the receiver 120a may perform the transmission and reception operations N times. In this regard, the term of 'repeatedly' refers to N times.

The B-flow image generator 214a may generate a B-flow image representing a tissue component and a blood flow component by using a plurality of echo signal groups. According to the present exemplary embodiment, the B-flow image generator 214a may sequentially generate a plurality of frames that constitute a B-flow image by iteratively using some of the plurality of echo signal groups.

In an exemplary embodiment, a B-flow image may be a black and white image in which a moving object is brighter than a stationary object. In another exemplary embodiment, a B-flow image may be a color image showing different colors representing a velocity or direction of a moving object. Such a B-flow technique provides clear images of blood vessels by reducing artificial materials within the blood vessels, thereby facilitating accurate diagnosis of lesions along walls of the blood vessels and/or within the blood vessels.

In particular, the B-flow image generator 214a may sequentially generate the plurality of frames by partially overlapping the plurality of echo signal groups. In an exemplary embodiment, the B-flow image generator 214a may sequentially generate first and second frames by using N echo signal groups and M echo signal group or groups acquired after obtaining the N echo signal groups, wherein M is a natural number less than N, for example, 1. In detail, the B-flow image generator 214a may generate the first frame by using the N echo signal groups and the second frame by using some of the N echo signal groups and by using the M echo signal groups. For example, the B-flow image generator 214a may generate the second frame by using N−M echo signal groups among the N echo signal groups and the M echo signal groups.

According to an exemplary embodiment, arbitrary ones of the N echo signal groups may be repeatedly used to generate the first and second frames. In another exemplary embodiment, echo signal groups acquired later among the N echo signal groups may be repeatedly used to generate the first and second frames. For example, the B-flow image generator 214a may generate the first frame by using first through Nth echo signal groups that are sequentially acquired and generate the second frame by using Nth−M echo signal group through Nth+M echo signal group that are sequentially acquired.

Figure 4:
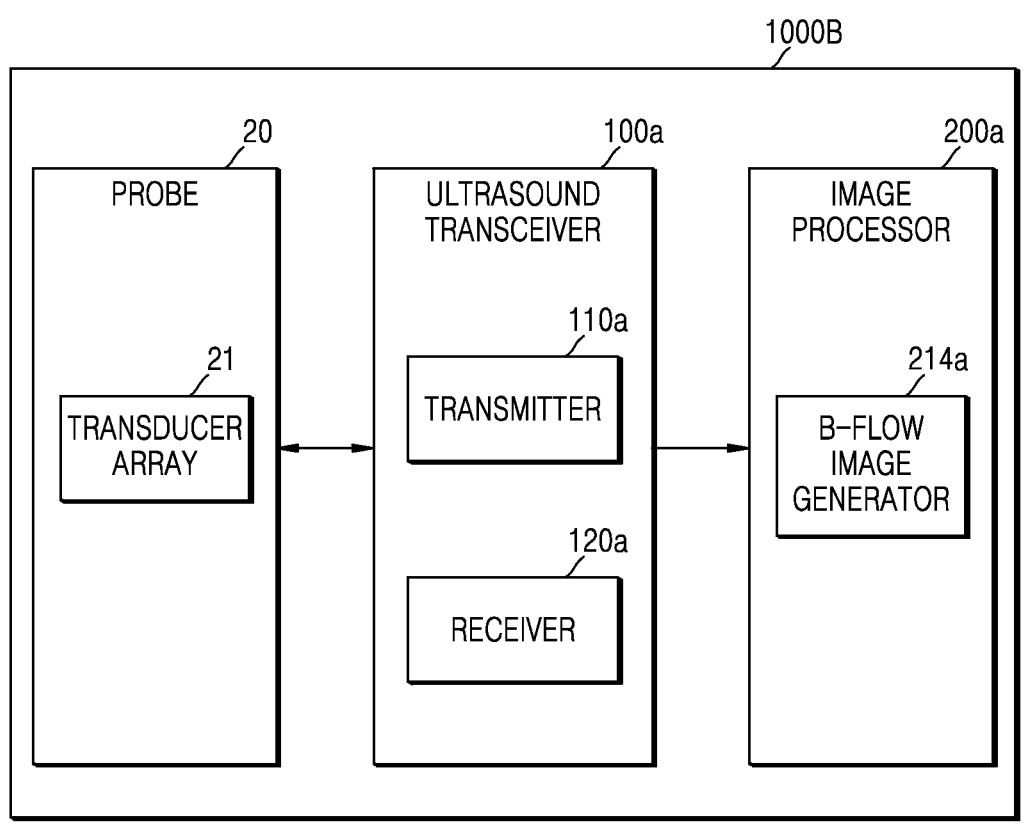
FIG. 4 is a block diagram of an ultrasound diagnostic apparatus according to an exemplary embodiment.

FIG. 4 is a block diagram of a configuration of an ultrasound diagnostic apparatus 1000B according to another exemplary embodiment.

Referring to FIG. 4, the ultrasound diagnostic apparatus 1000B according to the present exemplary embodiment may include a probe 20, an ultrasound transceiver 100a, and an image processor 200a. The ultrasound transceiver 100a may include a transmitter 110a and a receiver 120a, and the image processor 200a may include a B-flow image generator 214a. The descriptions above with respect to the ultrasound diagnostic apparatus 1000A may be applied to the ultrasound diagnostic apparatus 1000B.

Figure 5:
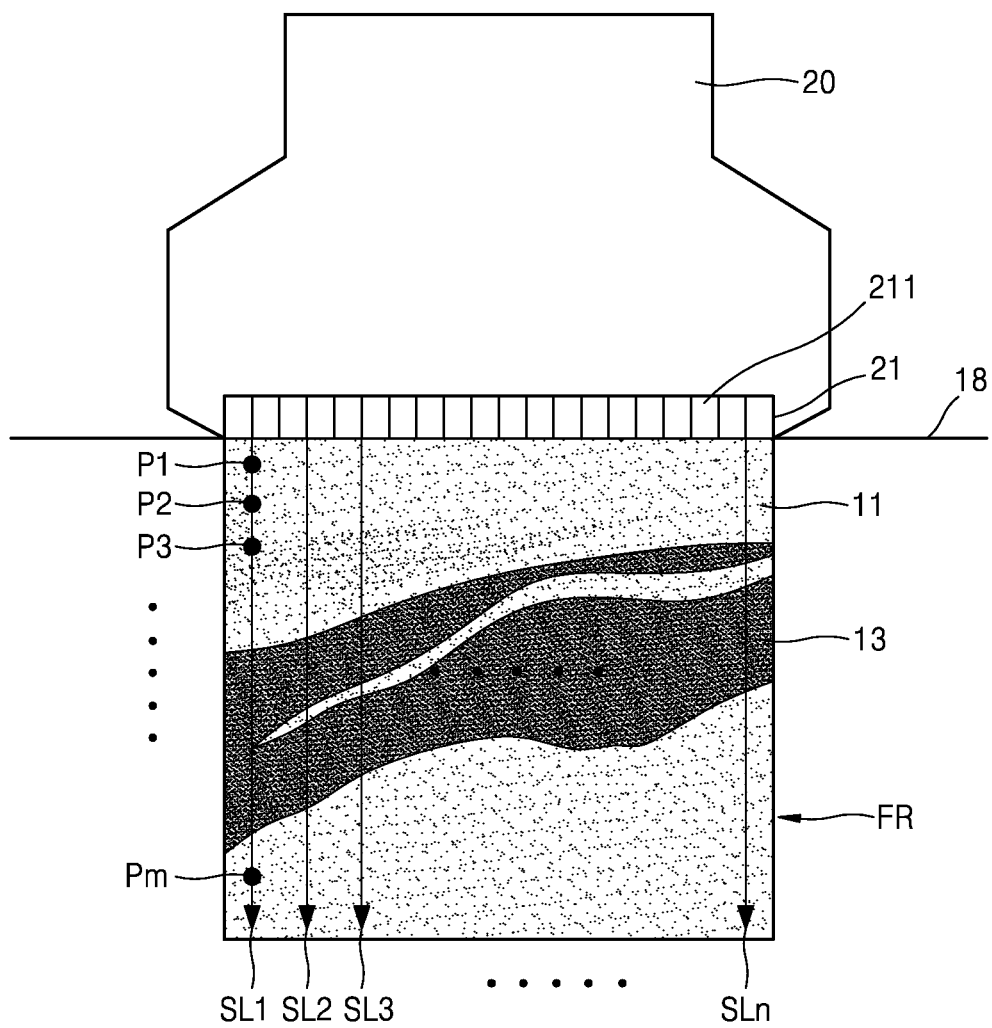
FIG. 5 is a diagram of a probe according to an exemplary embodiment.

FIG. 5 is a diagram of the probe 20 in the ultrasound diagnostic apparatus 1000B of FIG. 4, according to an exemplary embodiment.

Referring to FIG. 5, the probe 20 according to the present exemplary embodiment comes in contact with a surface 18 of an object 10 to transmit ultrasound signals to the object 10 and detect echo signals reflected therefrom. The probe 20 may include the transducer array 21 in which a plurality of transducers 211 are arranged. Each of the transducers 211 may include a piezoelectric element that generates an ultrasound signal from an electrical signal and detects an echo signal. The probe 20 may include a single array probe, a linear array probe, a curvilinear array probe, a phased array probe, an annular array probe, and a matrix array probe according to the arrangement of the piezoelectric elements.

The probe 20 may transmit an ultrasound signal to a plurality of scan lines SL1, SL2, and SL3 through SLn (where n is a natural number) set in the object 10 and acquire ultrasound image data for each of the scan lines SL1 through SLn based on an echo signal received in response to the transmitted ultrasound signal. The probe 20 may acquire data related to a plurality of sampling points P1, P2, and P3 through Pm (where m is a natural number) set on each of the scan lines SL1 through SLn from the echo signal corresponding to the scan line. Reference numeral 11 denotes tissue, reference numeral 13 denotes blood, and FR denotes a frame.

Figure 6:
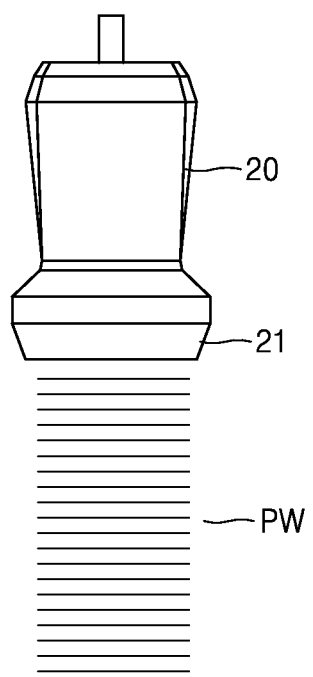
FIG. 6 illustrates an implementation example of the probe according to an exemplary embodiment.

FIG. 6 is an implementation example of the probe 20 of FIG. 5.

Referring to FIG. 6, the probe 20 may output an ultrasound signal PW having a waveform that is not focused on a focal point within an ultrasound image, e.g., having the form of a plane wave. In this case, a plurality of transducers in the transducer array 21 are simultaneously activated to output the ultrasound signal PW having the form of a plane wave.

The operation of the ultrasound diagnostic apparatus 1000B will now be described in detail with reference to FIGS. 4 through 6.

The transmitter 110a generates pulses for forming transmission ultrasound waves based on a predetermined PRF, determines a delay time for each of the plurality of transducers 211 in the probe 20, and applies a driving pulse to the plurality of transducers 211. In an exemplary embodiment, the transmitter 110a may determine a same delay time for the plurality of transducers 211 and apply a driving pulse substantially simultaneously thereto. In another exemplary embodiment, the transmitter 110a may determine a same delay time for some of the plurality of transducers 211, which are arranged adjacent to one another, and apply a driving pulse substantially simultaneously to the adjacently arranged transducers 211. In this way, according to the present exemplary embodiment, the plurality of transducers 211 may be activated substantially simultaneously to transmit an unfocused ultrasound signal, i.e., a plane wave signal, to the object 10.

The probe 20 may receive a driving pulse from the transmitter 110a, and some or all of the plurality of transducers may be activated in response to the driving pulse, i.e., the transducers may be activated to transmit an ultrasound signal and detect an echo signal.

The receiver 120a may receive a plurality of echo signals corresponding to the plurality of scan lines SL1 through SLn, and the plurality of echo signals are clustered into one echo signal group according to an echo signal received in response to a corresponding transmission signal. Each of the plurality of echo signals may include data related to the plurality of sampling points P1 through Pm set on a corresponding scan line.

The transmitter 110a and the receiver 120a may perform transmission and reception operations iteratively. For example, the transmitter 110a may sequentially transmit ultrasound signals, and the receiver 120a may sequentially receive echo signal groups corresponding to the respective transmission signals.

The B-flow image generator 214a may generate a B-flow image representing a tissue component and a blood flow component by using a plurality of echo signal groups. According to the present exemplary embodiment, the B-flow image generator 214a may sequentially generate a plurality of frames that constitute a B-flow image by iteratively using some of the plurality of echo signal groups.

In detail, the B-flow image generator 214a combines data related to a plurality of sampling points P1 through Pm on each scan line to thereby form B-flow image data for the scan line. For example, the B-flow image generator 214a may combine data related to a plurality of sampling points P1 through Pm set on a first scan line SL1 to thereby form ultrasound image data for the first scan line SL1. In this way, the B-flow image generator 214a may generate ultrasound image data for each of the plurality of scan lines SL1 through SLn and combine the generated ultrasound image data to generate a frame FR, i.e., an ultrasound image.

FIGS. 7A through 7D illustrate transmissions of ultrasound signals according to exemplary embodiments.

Figure 7A:
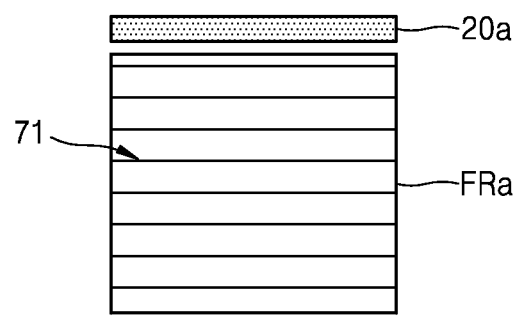
FIGS. 7A, 7B, 7C, and 7D illustrate transmissions of ultrasound signals according to exemplary embodiments.

Referring to FIG. 7A, a probe 20a may output a first ultrasound signal 71 having a waveform that is not focused on a focal point within an object, i.e., having the form of a plane wave. The first ultrasound signal 71 is substantially the same as the ultrasound signal PW shown in FIG. 6. In detail, a plurality of transducers in the probe 20a may be simultaneously activated to output the first ultrasound signal 71 having the form of a plane wave. In this way, an ultrasound image, i.e., a frame FRa, may be acquired by transmitting the first ultrasound signal 71 to a plurality of scan lines set in the object.

Figure 7B:
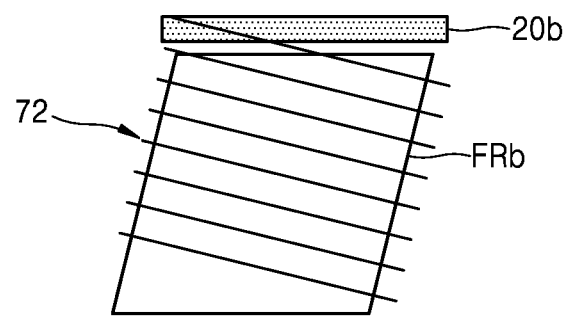

Referring to FIG. 7B, a probe 20b may output a second ultrasound signal 72 having the form of a plane wave that is not focused on a focal point within an object and tilted at a predetermined angle. In detail, a plurality of transducers in the probe 20b may be sequentially activated to output the second ultrasound signal 72 having the form of a plane wave tilted at the predetermined angle. In this way, an ultrasound image, i.e., a frame FRb, may be acquired by transmitting the second ultrasound signal 72 to a plurality of scan lines in the object, which are set at a predetermined steering angle.

Figure 7C:
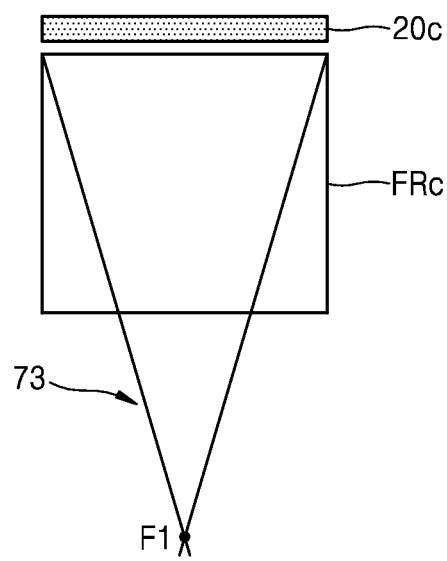

Referring to FIG. 7C, a probe 20c may output a third ultrasound signal 73 having the form of a plane wave that is focused into a far field within an object. In detail, a plurality of transducers in the probe 20c, to which different delay times are applied, may output the third ultrasound signal 73 that is focused on a focal point F1 outside a frame FRc. In this way, an ultrasound image, i.e., the frame FRc, may be acquired by transmitting the third ultrasound signal 73 to a plurality of scan lines set in the object.

Figure 7D:
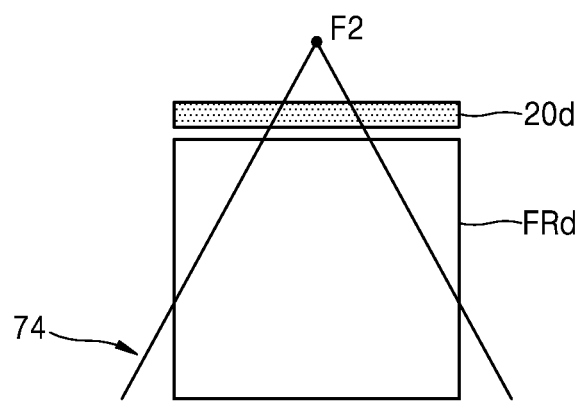

Referring to FIG. 7D, a probe 20d may output a fourth ultrasound signal 74 that is focused on a focal point F2 outside an object. In detail, a plurality of transducers in the probe 20d, to which different delay times are applied, may output the fourth ultrasound signal 74 that is focused on the focal point F2, e.g., facing a frame FRd. In this way, an ultrasound image, i.e., the frame FRd, may be acquired by transmitting the fourth ultrasound signal 74 to a plurality of scan lines set outside the object.

According to the exemplary embodiments described with reference to FIGS. 7A through 7D, the probe 20a, 20b, 20c, or 20d may transmit an ultrasound signal substantially simultaneously to a plurality of scan lines in an object and receive a plurality of echo signals respectively corresponding to the plurality of scan lines substantially simultaneously from the object. Thus, the echo signals corresponding to the scan lines may be simultaneously received by performing a single transmission/reception process. Thus, the amount of time required for generating one frame may be reduced, and a frame rate may be increased.

Figure 8:
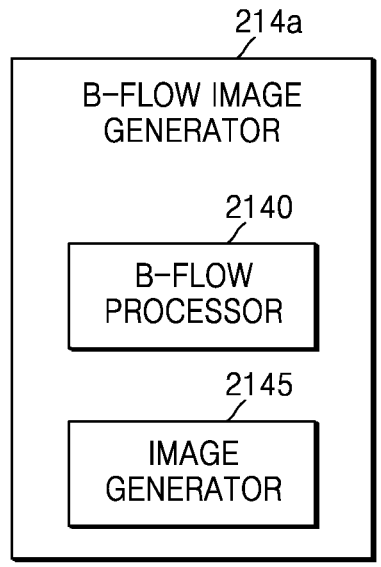
FIG. 8 illustrates a B-flow image generator according to an exemplary embodiment.

FIG. 8 illustrates a B-flow image generator 214a according to an exemplary embodiment.

Referring to FIG. 8, the B-flow image generator 214a according to the present exemplary embodiment may include a B-flow processor 2140 and an image generator 2145. The B-flow image generator 214a may be embodied in the ultrasound diagnostic apparatuses 1000A and 1000B of FIGS. 3 and 4.

The B-flow processor 2140 may extract B-flow data from a plurality of echo signals simultaneously received by the receiver 120a. In detail, the B-flow processor 2140 may extract B-flow data for each scan line by combining data related to a plurality of sampling points P1 through Pm on the scan line. For example, the B-flow processor 2140 may extract B-flow data for the first scan line SL1 from an echo signal corresponding to the first scan line SL1 by combining data related to a plurality of sampling points P1 through Pm on the first scan line SL1.

The B-flow processor 2140 may iteratively extract B-flow data from a plurality of echo signal groups sequentially received by the receiver 120*a*. For example, the B-flow processor 2140 may extract first B-flow data for a first scan line SL1 from an echo signal in a first echo signal group, corresponding to the first scan line SL1, and combine data related to a plurality of sampling points P1 through Pm on the first scan line SL1. The B-flow processor 2140 may also extract second B-flow data for a first scan line SL1 from an echo signal in a second echo signal group, corresponding to the first scan line SL1, by combining data related to a plurality of sampling points P1 through Pm on the first scan line SL1.

The image generator 2145 may generate a plurality of frames that constitute a B-flow image by using the extracted B-flow data. In detail, the image generator 2145 may generate a first frame from sequentially acquired first through Nth echo signals by combining B-flow data for each scan line. In this case, the image generator 2145 may generate scan line images for a plurality of scan lines and combine the generated scan line images to generate the first frame.

For example, the image generator 2145 may generate a scan line image for a first scan line SL1 by combining first through Nth B-flow data for the first scan line SL1. Similarly, the image generator 2145 may generate a scan line image for a second scan line SL2 by combining first through Nth B-flow data for the second scan line SL2. The image generator 2145 may also generate a scan line image for a third scan line SL3 by combining first through Nth B-flow data for the third scan line SL3. In this way, the image generator 2145 may generate the scan line images for the first through third scan lines SL1 through SL3 and combine the generated scan line images to generate a first frame.

Subsequently, the image generator 2145 may generate a second frame from sequentially acquired Nth−M through Nth+M echo signals by combining B-flow data for each scan line. In this way, the image generator 2145 may generate the second frame by partially overlapping a plurality of echo signals used to generate the first frame.

For example, the image generator 2145 may generate a scan line image for the first scan line SL1 by combining second through Nth+1 B-flow data for the first scan line SL1. Similarly, the image generator 2145 may generate a scan line image for the second scan line SL2 by combining second through Nth+1 B-flow data for the second scan line SL2. The image generator 2145 may also generate a scan line image for the third scan line SL3 by combining second through Nth+1 B-flow data for the third scan line SL3. In this way, the image generator 2145 may generate the scan line images for the first through third scan lines SL1 through SL3 and combine the generated scan line images to generate a second frame.

Figure 9:
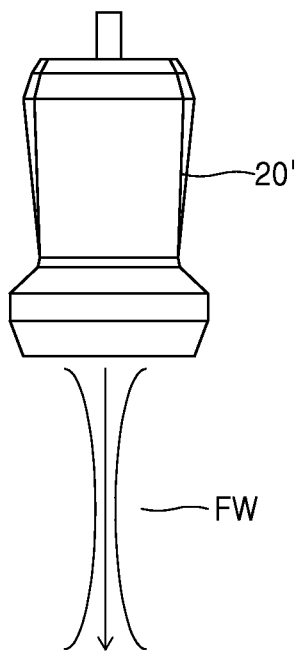
FIG. 9 illustrates a probe according to a related art.

FIG. 9 illustrates a probe 20' to a related art.

Referring to FIG. 9, the probe 20' may output an ultrasound signal FW having a focused waveform. In this case, some of a plurality of transducers in the probe 20' may be activated, and different delay times may be applied to the activated transducers. Thus, the probe 20' may output the ultrasound signal FW having a focused waveform.

FIGS. 10A, 10B, 10C, and 10D illustrate transmission and reception of an ultrasound signal via the probe 20' of FIG. 9.

Figure 10A:
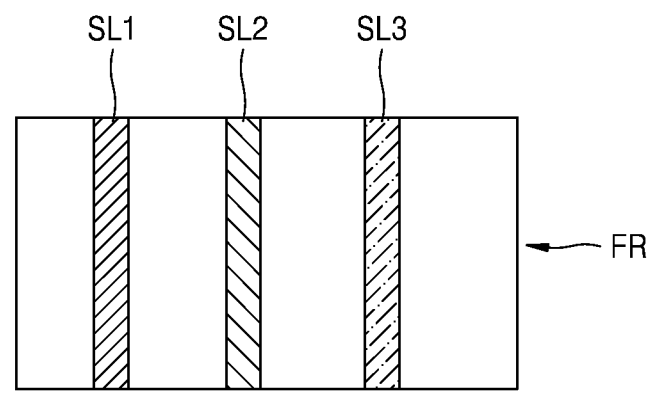
FIGS. 10A, 10B, 10C, and 10D illustrate transmission and reception of an ultrasound signal.

Referring to FIG. 10A, a frame FR may include first through third scan lines SL1 through SL3. For example, the frame FR may be generated by combining ultrasound image data for the first through third scan lines SL1 through SL3. However, this is only an example for convenience of explanation, and the frame FR may include four or more scan lines.

Figure 10B:
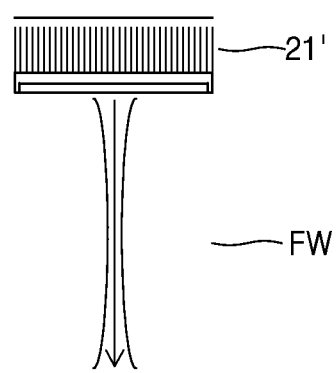

Referring to FIG. 10B, the probe 20' may include a transducer array 21', and some of a plurality of transducers in the transducer array 21' may output an ultrasound signal FW having a focused waveform by respectively receiving driving pulses to which different delay times are applied.

Figure 10C:
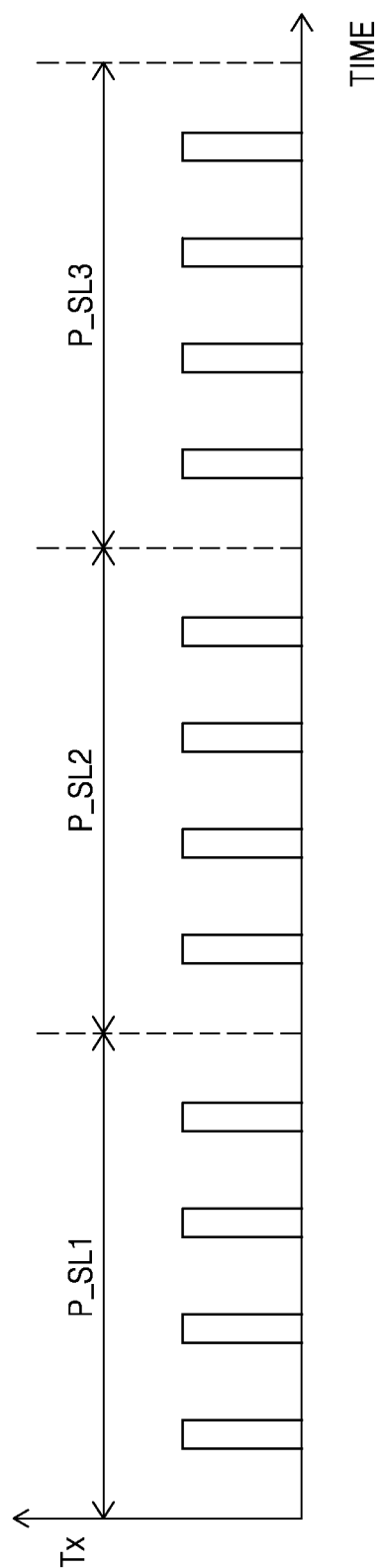

Referring to FIG. 10C, Y-axis represents the magnitude of an ultrasound signal Tx being transmitted from the probe 20' and X-axis represents time. The probe 20' may repeat a transmission/reception process N times for each scan line wherein N is the number of ensembles. For example, if the number N of ensembles is 4, the probe 20' may transmit an ultrasound signal Tx four times for each scan line.

An interval during which first through fourth ultrasound signals for a first scan line SL1 are transmitted, an interval during which fifth through eighth ultrasound signals for a second scan line SL2 are transmitted, and an interval during which ninth through twelfth ultrasound signals for a third scan line SL3 are transmitted are referred to as a first interval P_SL1, a second interval P_SL2, and a third interval P_SL3, respectively.

During the first interval P_SL1, transducers corresponding to the first scan line SL1 are activated to transmit an ultrasound signal FW having a focused waveform to the first scan line SL1. During the second interval P_SL2, transducers corresponding to the second scan line SL2 are activated to transmit an ultrasound signal FW having a focused waveform to the second scan line SL2. During the third interval P_SL3, transducers corresponding to the third scan line SL3 are activated to transmit an ultrasound signal FW having a focused waveform to the third scan line SL3.

Figure 10D:
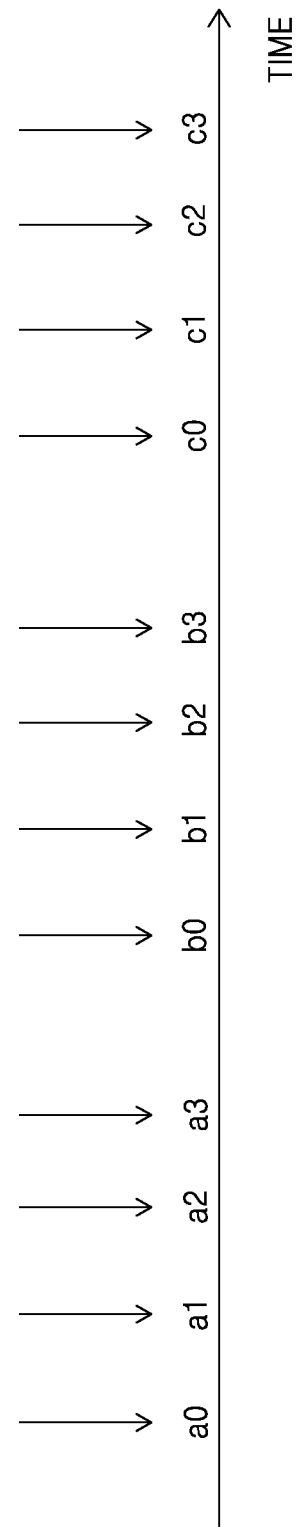

FIG. 10D illustrates a process of receiving echo signals over time. In this case, a0 through a3 denote echo signals corresponding to a first scan line SL1 which are received in response to first through fourth ultrasound signals, respectively, b0 through b3 represent echo signals corresponding to a second scan line SL2 which are received in response to fifth through eighth ultrasound signals, respectively, and c0 through c3 denote echo signals corresponding to a third scan line SL3 which are received in response to ninth through twelfth ultrasound signals, respectively.

As described above, when the probe 20' outputs an ultrasound signal FW having a focused waveform, N transmission/reception processes corresponding to the number of ensembles are required for each scan line to generate one frame. Thus, the amount of time needed to generate one frame is proportional to the product of the number L of scan lines and the number N of ensembles (i.e., L×N). In the present example, to generate a single frame, the transmission/reception process needs to be performed sequentially 4 times for each of the first through third scan lines SL1 through SL3, i.e., a total of 12 times.

Figure 11A:
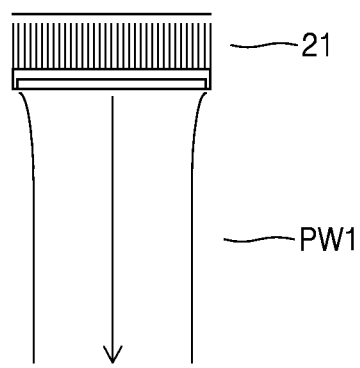
FIGS. 11A, 11B, and 11C illustrate transmission and reception of an ultrasound signal, according to an exemplary embodiment.
Figure 11B:
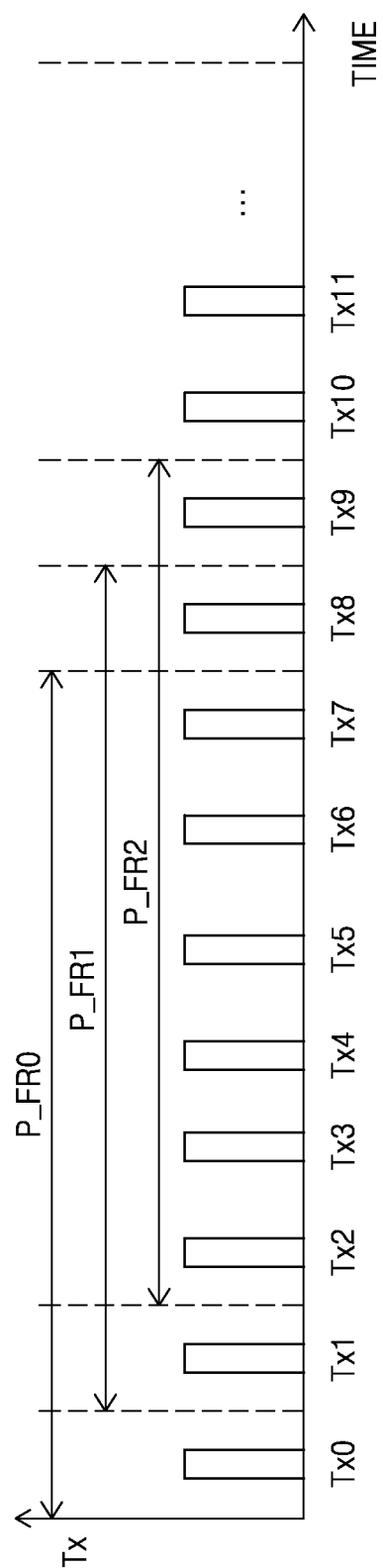
Figure 11C:
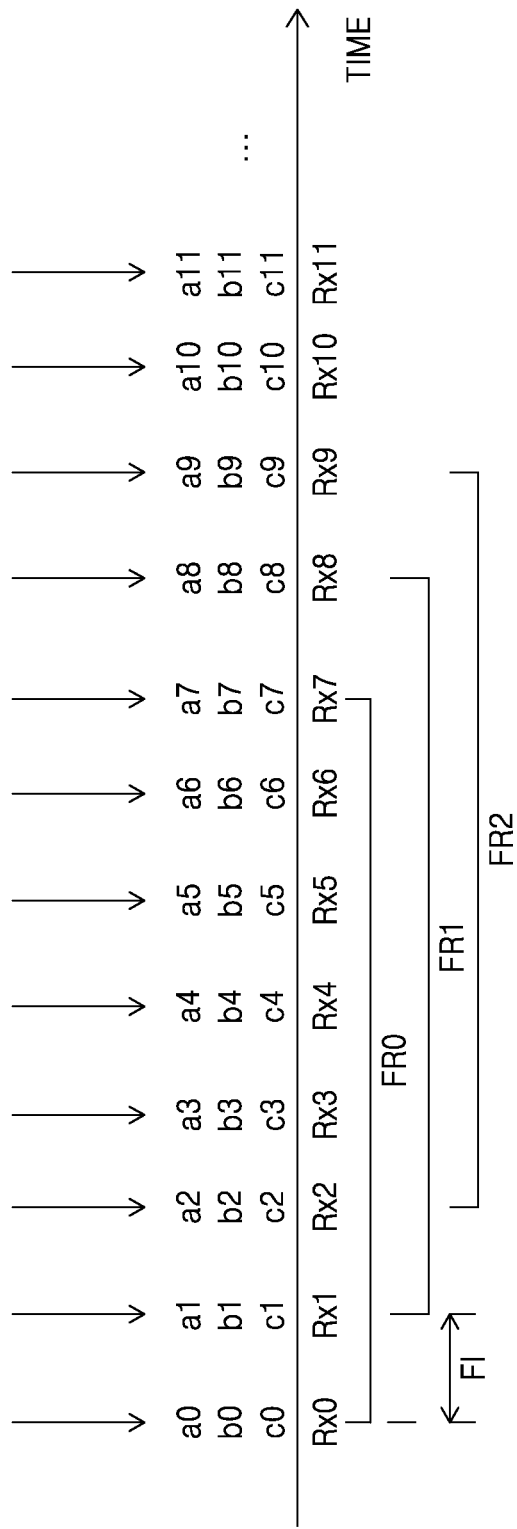

FIGS. 11A, 11B, and 11C illustrate transmission and reception of an ultrasound signal via the probe 20 of FIG. 6, according to an exemplary embodiment.

Referring to FIG. 11A, the probe 20 may include the transducer array 21, and each of a plurality of transducers in the transducer array 21 may output an ultrasound signal PW1 having the form of an unfocused plane wave by receiving a driving pulse to which the same delay time is applied.

Referring to FIG. 11B, the Y-axis denotes the magnitude of an ultrasound signal Tx being transmitted by the probe 20 and the X-axis denotes time. The probe 20 may perform a transmission/reception process N times for the first through third scan lines SL1 through SL3, to generate a frame. In the present exemplary embodiment, the number N of ensembles is 8, and the probe 20 may transmit an ultrasound signal Tx eight times for the first through third scan lines SL1 through SL3, for example, shown in FIG. 10A.

An image quality of a region of interest (ROI) generated by using the ultrasound signal PW1 having the form of an unfocused plane wave may be lower than an image quality of a ROI generated by using a ultrasound signal FW having a focused waveform of FIG. 10B. In the present exemplary embodiment, the number N of ensembles in case of the ultrasound signal PW1 may be more than the number N of ensembles in case of the ultrasound signal FW in order to improve the image quality. Accordingly, the image quality of the ROI generated by using the ultrasound signal PW1 may be improved.

An interval during which first through eighth ultrasound signals Tx0 through Tx7 for a first frame FR0 are transmitted, an interval during which second through ninth ultrasound signals Tx1 through Tx8 for a second frame FR1 are transmitted, and an interval during which third through tenth ultrasound signals Tx2 through Tx9 for a third frame FR2 are transmitted are a first interval P_FR0, a second interval P_FR1, and a third interval P_FR2, respectively.

According to the present exemplary embodiment, since the number N of ensembles is 8, the first interval P_FR0 may include eight ultrasound signals Tx0 through Tx7. However, exemplary embodiments are not limited thereto. In other exemplary embodiments, if the number N of ensembles is less than 8, the first interval P_FR0 may include a number of ultrasound signals fewer than 8. If the number N of ensembles is greater than 8, the first interval P_FR0 may include a number of ultrasound signals greater than 8.

In the present exemplary embodiment, M is equal to 1, and the second interval P_FR1 may include the second through ninth ultrasound signals Tx1 through Tx8. However, exemplary embodiments are not limited thereto. In other exemplary embodiments, if M is 2, the second interval P_FR1 may include third through tenth ultrasound signals Tx2 through Tx9. If M is 3, the second interval P_FR1 may include fourth through eleventh ultrasound signals Tx3 through Tx10.

During each of the first through third intervals P_FR0 through P_FR2, the transducers in the transducer array 21 are all activated to transmit an ultrasound signal PW1 having the form of a plane wave to the first through third scan lines SL1 through SL3. In this case, the first through eighth ultrasound signals Tx0 through Tx7, the second through ninth ultrasound signals Tx1 through Tx8, and the third through tenth ultrasound signals Tx2 through Tx9 are used to generate the first frame FR0, the second frame FR1, and the third frame FR2, respectively.

FIG. 11C illustrates a process of receiving echo signals over time. In this case, as first through twelfth ultrasound signals Tx0 through Tx11 are sequentially transmitted, first through twelfth echo signal groups Rx0 through Rx11 are sequentially received. In FIG. 11C, a0 through a11 denote echo signals corresponding to a first scan line SL1 which are sequentially received, b0 through b11 represent echo signals corresponding to a second scan line SL2 which are sequentially received, and c0 through c11 denote echo signals corresponding to a third scan line SL3 which are sequentially received.

The first echo signal group Rx0 is a group of echo signals received in response to the first ultrasound signal Tx0 and includes echo signals a0, b0, and c0 corresponding to first through third scan lines SL1 through SL3, respectively. The second echo signal group Rx1 is a group of echo signals received in response to the second ultrasound signal Tx1 and includes echo signals a1, b1, and c1 corresponding to first through third scan lines SL1 through SL3, respectively.

According to the present exemplary embodiment, the receiver 120a may simultaneously receive echo signals corresponding to a plurality of scan lines, e.g., SL1 through SL3, in response to an ultrasound signal. The simultaneously received echo signals at each receiver channel may constitute a single echo signal group. Thus, the amount of time required to generate one frame may be substantially reduced, and accordingly, a frame rate may be substantially improved.

When the probe 20 outputs an ultrasound signal PW1 having the form of a plane wave according to the present exemplary embodiment, echo signals for all scan lines may be received simultaneously via a single transmission/reception process. Accordingly, one frame may be generated by performing a transmission/reception process N times corresponding to the number of ensembles, regardless of the number L of scan lines. Thus, the amount of time needed to generate one frame is proportional to the number N of ensembles without regard to the number L of scan lines. In the present exemplary embodiment, to generate a single frame, the transmission/reception process needs to be performed 8 times simultaneously for the first through third scan lines SL1 through SL3, i.e., a total of 8 times.

If the number of ensembles in the present exemplary embodiment is equal to that of an ultrasound signal FW having a focused waveform, as described above with reference to FIG. 9, the transmission of an ultrasound signal PW1 having the form of a plane wave according to the present exemplary embodiment needs to be repeated a fewer number of times than the transmission of an ultrasound signal FW. Thus, a frame rate may be substantially enhanced.

Further, for the same amount of time needed to generate a single frame by transmitting an ultrasound signal FW, as described with reference to FIG. 9, and by transmitting an ultrasound signal PW1 according to an exemplary embodiment, a much greater number of ensembles may be used in an exemplary embodiment than that when transmitting an ultrasound signal FW described with reference to FIG. 9. Thus, the quality of a B-flow image may be substantially improved.

In the present exemplary embodiment, a plurality of frames may be sequentially generated by partially overlapping the plurality of echo signal groups. In particular, first through eighth echo signal groups Rx0 through Rx7, second through ninth echo signal groups Rx1 through Rx8, and third through tenth echo signal groups Rx2 through Rx9 may be used to generate the first frame FR0, the second frame FR1, and the third frame FR2, respectively. In this case, the second through eighth echo signal groups Rx1 through Rx7 may be repeatedly used to generate the first and second frames FR0 and FR1. Further, the third through eighth echo signal groups Rx2 through Rx7 may be repeatedly used to generate the first and third frames FR0 and FR2. Thus, since the amount of time required to generate a new frame may be substantially reduced, a frame rate may be enhanced.

FIGS. 12A, 12B, 12C, and 12D illustrate transmission and reception of an ultrasound signal via the probe 20 of FIG. 6, according to another exemplary embodiment.

Figure 12A:
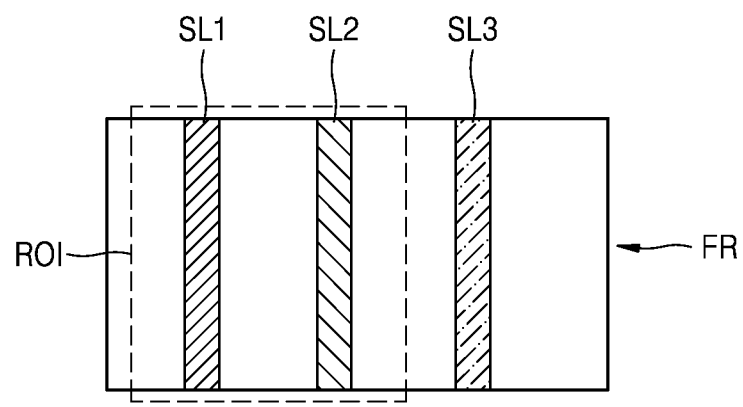
FIGS. 12A, 12B, 12C, and 12D illustrate transmission and reception of an ultrasound signal, according to an exemplary embodiment.

Referring to FIG. 12A, a frame FR may include first through third scan lines SL1 through SL3. In the present exemplary embodiment, the first and second scan lines SL1 and SL2 may be scan lines corresponding to a ROI. Thus, an image of the ROI may be generated by combining ultrasound image data for first and second scan lines SL1 and SL2. However, this is only an example for convenience of explanation, and the ROI may include three or more scan lines.

Figure 12B:
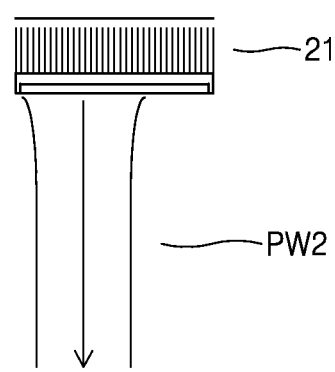

Referring to FIG. 12B, the probe 20 may include the transducer array 21, and some of a plurality of transducers in the transducer array 21 corresponding to the ROI may output an ultrasound signal PW2 having the form of an unfocused plane wave by receiving a driving pulse to which the same delay time is applied.

Figure 12C:
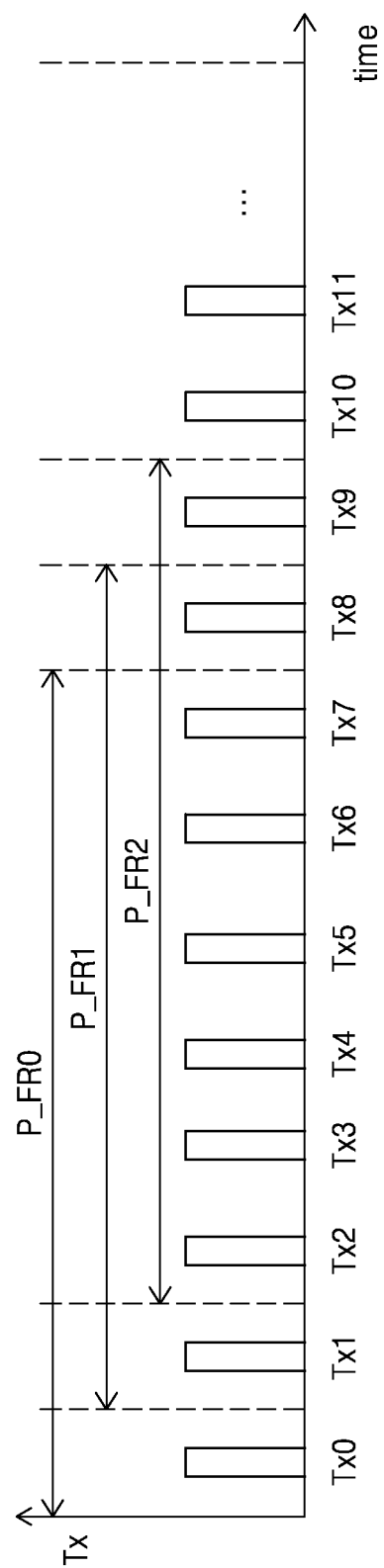

Referring to FIG. 12C, the Y-axis represents the magnitude of an ultrasound signal Tx being transmitted by the probe 20 and the X-axis represents time. The probe 20 may perform a transmission/reception process N times through each scan line. For example, if the number N of ensembles is 8, the probe 20 may transmit an ultrasound signal Tx eight times for each scan line, to generate a frame.

During the first through third intervals P_FR0 through P_FR2, transducers in the transducer array 21 corresponding to first and second scan lines SL1 and SL2 are all activated to transmit an ultrasound signal PW2 having the form of a plane wave to the first and second scan lines SL1 and SL2. In this case, the first through eighth ultrasound signals Tx0 through Tx7, the second through ninth ultrasound signals Tx1 through Tx8, and the third through tenth ultrasound signals Tx2 through Tx9 are used to generate the first frame FR0, the second frame FR1, and the third frame FR2, respectively.

Figure 12D:
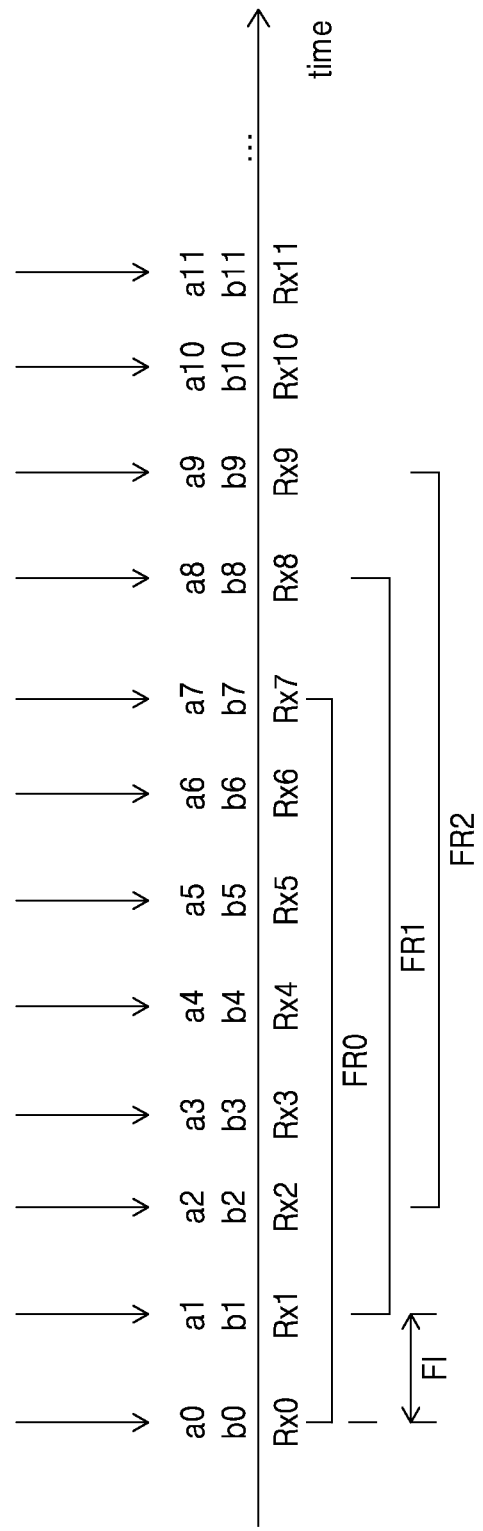

FIG. 12D illustrates a process of receiving echo signals over time. In this case, as first through twelfth ultrasound signals Tx0 through Tx11 are sequentially transmitted, first through twelfth echo signal groups Rx0 through Rx11 are sequentially received. In FIG. 12D, a0 through a11 denote echo signals corresponding to a first scan line SL1 which are sequentially received, and b0 through b11 represent echo signals corresponding to a second scan line SL2 which are sequentially received.

The first echo signal group Rx0 is a group of echo signals received in response to the first ultrasound signal Tx0 and includes echo signals a0 and b0 corresponding to the first and second scan lines SL1 and SL2, respectively, the second echo signal group Rx1 is a group of echo signals received in response to the second ultrasound signal Tx1 and includes echo signals a1 and b1 corresponding to the first and second scan lines SL1 and SL2, respectively, etc.

According to the present exemplary embodiment, the receiver 120a may simultaneously receive echo signals corresponding to a plurality of scan lines, e.g., SL1 and SL2, on an ROI in response to an ultrasound signal. The simultaneously received echo signals may be combined into a single echo signal group. Thus, the amount of time required to generate one frame including the ROI may be substantially reduced, and accordingly, a frame rate may be substantially improved.

When the probe 20 outputs an ultrasound signal PW2 having the form of a plane wave according to the present exemplary embodiment, echo signals for scan lines on an ROI may be received simultaneously via a single transmission/reception process. Accordingly, one frame may be generated by performing a transmission/reception process N times corresponding to the number of ensembles, regardless of the number L of scan lines. Thus, the amount of time needed to generate one frame is proportional to the number N of ensembles without regard to the number L of scan lines. In the present exemplary embodiment, to generate a single frame, the transmission/reception process needs to be performed 8 times simultaneously for the first and second scan lines SL1 and SL2, i.e., a total of 8 times.

In the present exemplary embodiment, a plurality of frames may be sequentially generated by partially overlapping the plurality of echo signal groups. In particular, first through eighth echo signal groups Rx0 through Rx7, second through ninth echo signal groups Rx1 through Rx8, and third through tenth echo signal groups Rx2 through Rx9 may be used to generate the first frame FR0, the second frame FR1, and the third frame FR2, respectively. In this case, the second through eighth echo signal groups Rx1 through Rx7 may be repeatedly used to generate the first and second frames FR0 and FR1. The third through eighth echo signal groups Rx2 through Rx7 may also be repeatedly used to generate the first and third frames FR0 and FR2. Thus, since the amount of time required to generate a new frame may be substantially reduced, a frame rate may be enhanced.

Figure 13:
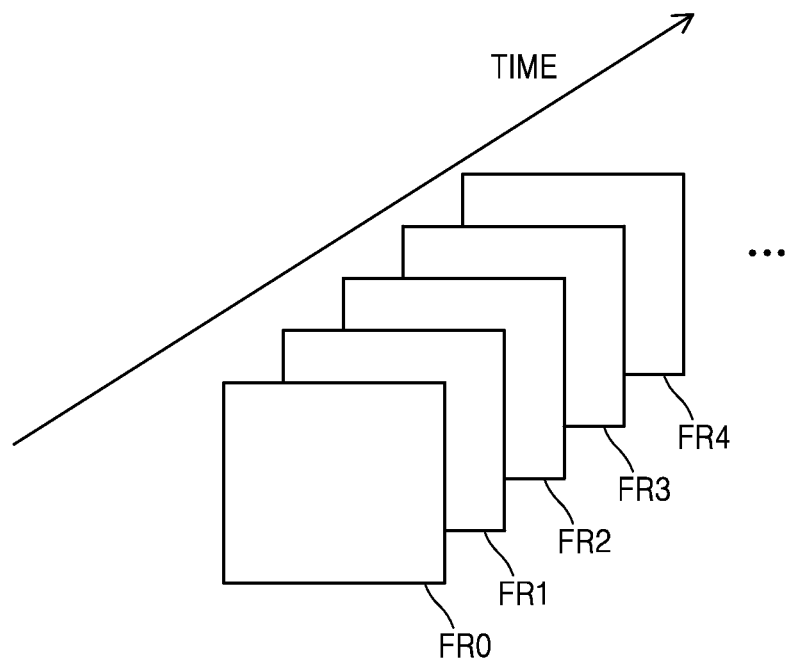
FIG. 13 illustrates a plurality of frames generated according to an exemplary embodiment.

FIG. 13 illustrates a plurality of frames generated according to an exemplary embodiment.

Referring to FIG. 13, first through fifth frames FR0 through FR4 are sequentially generated over time. As described above, according to an exemplary embodiment, some of a plurality of echo signal groups used to generate the first frame FR0 may be repeatedly used to generate the second frame FR1, and thus, a frame rate may be improved.

As data used to generate one frame is repeatedly used in generating a subsequent frame according to the present exemplary embodiment, an interval FI between the two frames may be decreased, and accordingly, an image of a blood flow may be monitored in real-time. Thus, the quality of a B-flow image may be further improved.

Figure 14:
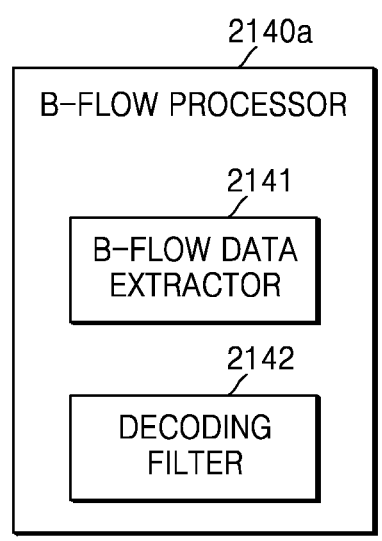
FIG. 14 illustrates a B-flow processor according to an exemplary embodiment.

FIG. 14 illustrates a B-flow processor 2140a according to an exemplary embodiment.

Referring to FIG. 14, the B-flow processor 2140a according to the present exemplary embodiment may include a B-flow data extractor 2141 and a decoding filter 2142. The B-flow processor 2140a may be embodied in the B-flow image generator 214a of FIG. 8.

The B-flow data extractor 2141 may extract B-flow data from a plurality of echo signals simultaneously received by the receiver 120a. In detail, the B-flow data extractor 2141 may extract B-flow data for each scan line by combining data related to a plurality of sampling points P1 through Pm on the scan line. For example, the B-flow data extractor 2141 may extract B-flow data for a first scan line SL1 from an echo signal corresponding to the first scan line SL1 by combining data related to a plurality of sampling points P1 through Pm on the first scan line SL1.

The B-flow data extractor 2141 may iteratively extract B-flow data from a plurality of echo signal groups sequentially received by the receiver 120a. For example, the B-flow data extractor 2141 may extract first B-flow data for a first scan line SL1 from an echo signal in a first echo signal group, corresponding to the first scan line SL1, by combining data related to a plurality of sampling points P1 through Pm on the first scan line SL1. The B-flow data extractor 2141 may also extract second B-flow data for a first scan line SL1 from an echo signal in a second echo signal group, corresponding to the first scan line SL1, by combining data related to a plurality of sampling points P1 through Pm on the first scan line SL1.

The decoding filter 2142 may perform decoding filtering on the extracted B-flow data, to attenuate a signal corresponding to a tissue component and enhance a signal corresponding to a blood flow component.

Figure 15:
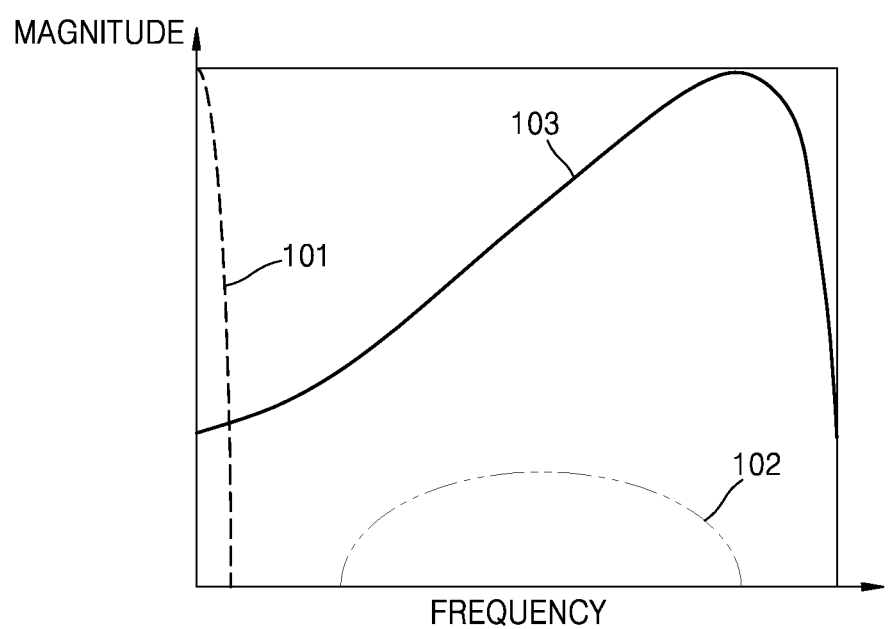
FIG. 15 is a graph for explaining the operation of a decoding filter according to an exemplary embodiment.

FIG. 15 is a graph for explaining the operation of the decoding filter 2142 according to an exemplary embodiment.

Referring to FIG. 15, the ordinate represents the magnitude of a reflected signal and the abscissa represents a frequency. A graph of a signal 101 represents a magnitude of a signal reflected from a tissue component (e.g., reference numeral 11 of FIG. 5) with respect to frequency, a graph of a signal 102 represents a magnitude of a signal reflected from a blood flow component (e.g., reference numeral 13 of FIG. 5), and a graph 103 represents filtering characteristics of the decoding filter 2142.

The signal 101 from the tissue component 11 may have a relatively high magnitude at a lower frequency while the signal 102 reflected from the blood flow component 13 has a relatively low magnitude at a higher frequency. For example, the signal reflected from the blood flow component 13 may have a magnitude that is about $1/100$ to about $1/1000$ that of the signal reflected from the tissue component 11. Thus, it is difficult to recognize the blood flow component 13 in a general B-mode image.

The decoding filter 2142 according to the present exemplary embodiment may perform decoding filtering to increase the magnitude of the signal 102 reflected from the blood flow component 13 while decreasing a magnitude of the signal 101 reflected from the tissue component 11. In detail, the decoding filter 2142 may perform decoding filtering by applying a weighted sum to a plurality of echo signals for each scan line, to attenuate the signal 101 corresponding to the tissue component 11 among the plurality of echo signals and increase the signal 102 corresponding to the blood flow component 13.

For example, the decoding filter 2142 may perform decoding filtering on a first scan line SL1 by applying different weighting factors to the first through eighth echo signals a0 through a7 corresponding to the first scan line SL1. The decoding filter 2142 may also perform decoding filtering on a second scan line SL2 by applying different weighting factors to the first through eighth echo signals b0 through b7 corresponding to the second scan line SL2. Similarly, the decoding filter 2142 may perform decoding filtering on a third scan line SL3 by applying different weighting factors to the first through eighth echo signals c0 through c7 corresponding to the third scan line SL3.

The image generator 2145 may generate scan line images for the first through third scan lines SL1 through SL3, respectively, based on the result of decoding filtering on the first through third scan lines SL1 through SL3, and combine the generated scan line images to generate a single frame.

According to exemplary embodiments, since the ultrasound diagnostic apparatuses 1000A and 1000B are configured to simultaneously receive echo signals for a plurality of scan lines by transmitting an ultrasound signal having the form of a plane wave, the number of ensembles may be increased. Accordingly, the order of the decoding filter 2142 can be increased, and thus, the resolution of a B-flow image may be enhanced.

Figure 16A:
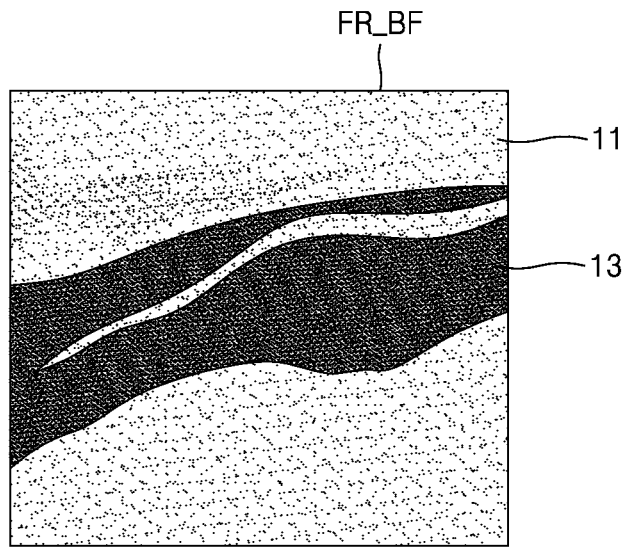
FIG. 16A illustrates a frame before undergoing decoding filtering.
Figure 16B:
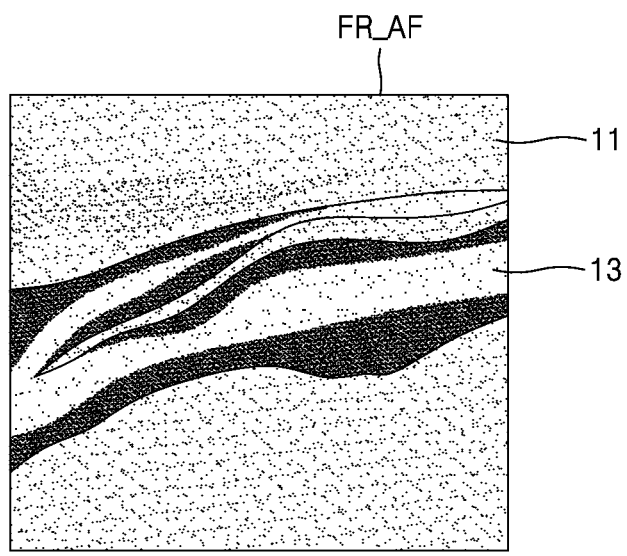
FIG. 16B illustrates a frame after undergoing decoding filtering according to an exemplary embodiment.

FIG. 16A illustrates a frame FR_BF before undergoing decoding filtering, and FIG. 16B illustrates a frame FR_AF after undergoing decoding filtering according to an exemplary embodiment.

Referring to FIG. 16A, in the frame FR_BF that has not undergone decoding filtering, a tissue component 11 appears bright while a blood flow component 13 appears dark, and thus a flow of blood cannot be observed. On the other hand, referring to FIG. 16B, in the frame FR_AF after undergoing decoding filtering, both a tissue component 11 and a blood flow component 13 appear bright, and thus, a flow of blood can be observed.

Figure 17:
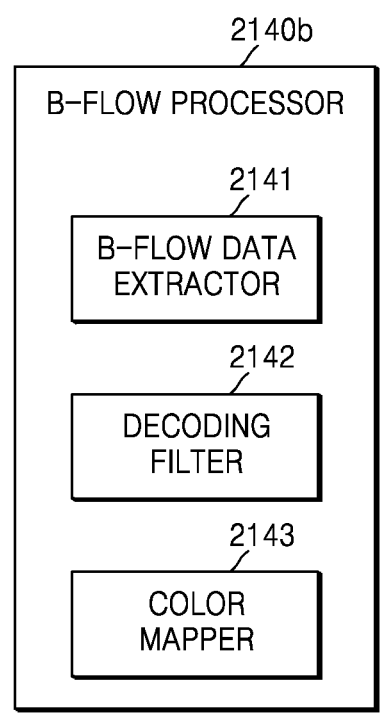
FIG. 17 is a block diagram of a B-flow processor according to an exemplary embodiment.

FIG. 17 is a block diagram of a B-flow processor 2140b according to another exemplary embodiment.

Referring to FIG. 17, the B-flow processor 2140b according to the present exemplary embodiment may include a B-flow data extractor 2141, a decoding filter 2142, and a color mapper 2143. The B-flow processor 2140b may be embodied in the B-flow image generator 214a of FIG. 8.

Further, the descriptions above with respect to the B-flow processor 2140a of FIG. 14 may be applied to the present exemplary embodiment. The B-flow processor 2140b may further include the color mapper 2143 in comparison to the B-flow processor 2140a of FIG. 14.

The color mapper 2143 may perform color mapping on B-flow data extracted by the B-flow data extractor 2141 or the result of decoding filtering output from the decoding filter 2142. Thus, the image generator 2145 may generate a B-flow image as a color image.

Figure 18:
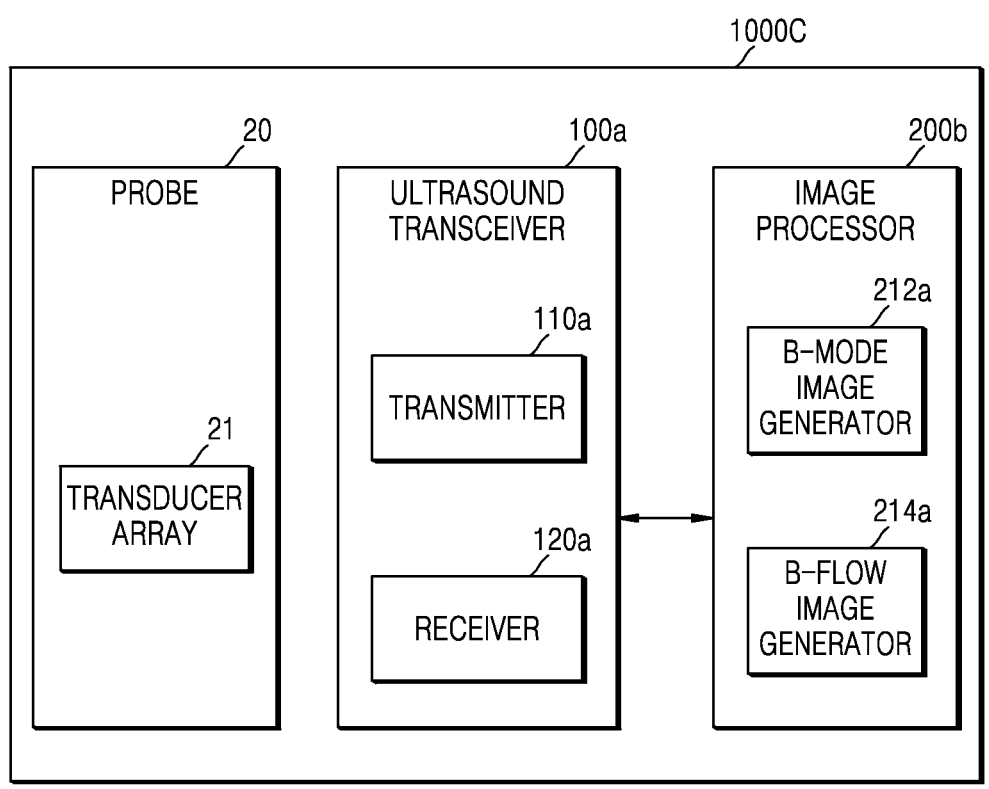
FIG. 18 is a block diagram of a configuration of an ultrasound diagnostic apparatus according to an exemplary embodiment.

FIG. 18 is a block diagram of a configuration of an ultrasound diagnostic apparatus 1000C according to another exemplary embodiment.

Referring to FIG. 18, the ultrasound diagnostic apparatus 1000C according to the present exemplary embodiment may include a probe 20, an ultrasound transceiver 100a, and an image processor 200b. The probe 20 may include a transducer array 21, and the ultrasound transceiver 100a may include a transmitter 110a and a receiver 120a. The descriptions above with respect to the ultrasound diagnostic apparatuses 1000B and 1000A may be applied to the ultrasound diagnostic apparatus 1000C.

The probe 20 and the ultrasound transceiver 100a may have substantially the same configurations as those described above with respect to the ultrasound diagnostic apparatuses 1000B and 1000A.

The image processor 200b may include a B-mode image generator 212a and a B-flow image generator 214a. The B-mode image generator 212a may extract B-mode data from a plurality of echo signals and generate a B-mode image based on the extracted B-mode data.

Figure 19:
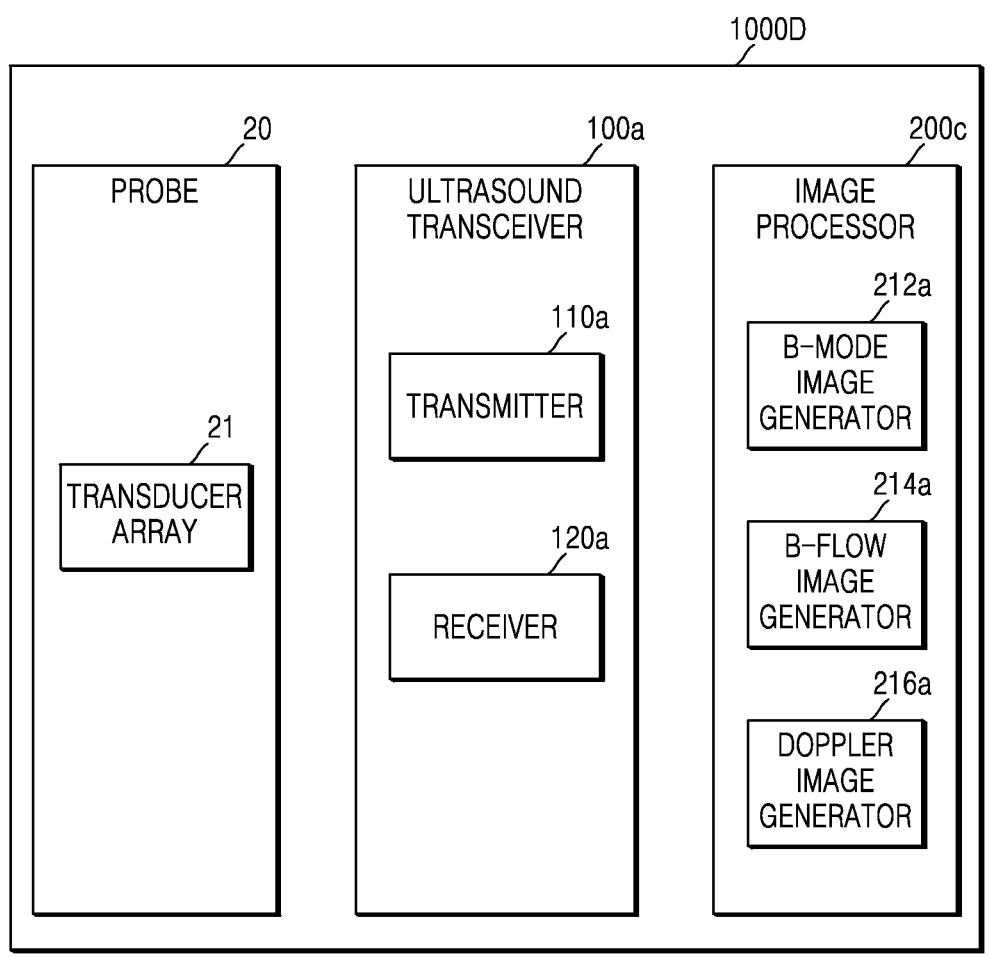
FIG. 19 is a block diagram of a configuration of an ultrasound diagnostic apparatus according to an exemplary embodiment.

FIG. 19 is a block diagram of a configuration of an ultrasound diagnostic apparatus 1000D according to another exemplary embodiment.

Referring to FIG. 19, the ultrasound diagnostic apparatus 1000D according to the present exemplary embodiment may include a probe 20, an ultrasound transceiver 100a, and an image processor 200c. The probe 20 may include a transducer array 21, and the ultrasound transceiver 100a may include a transmitter 110a and a receiver 120a. The descriptions with respect to the ultrasound diagnostic apparatuses 1000A, 1000B, and 1000C may be applied to the ultrasound diagnostic apparatus 1000D.

The probe 20 and the ultrasound transceiver 100a may have substantially the same configurations as those described above with respect to the ultrasound diagnostic apparatuses 1000A, 1000B, and 1000C.

The image processor 200c may include a B-mode image generator 212a, a B-flow image generator 214a, and a Doppler image generator 216a. The B-mode image generator 212a may extract B-mode data from a plurality of echo signals and generate a B-mode image based on the extracted B-mode data. The Doppler image generator 216a may extract Doppler data from a plurality of echo signals, and generate a Doppler image based on the extracted Doppler data.

Figure 20:
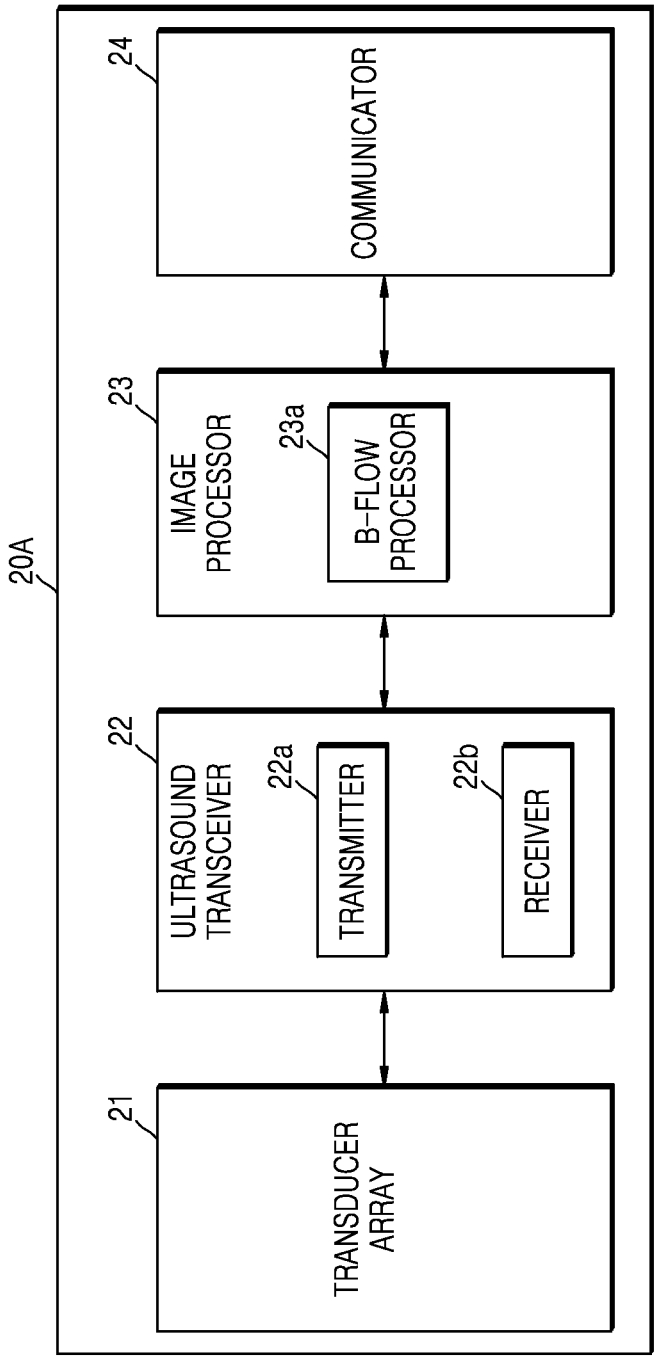
FIG. 20 is a block diagram of a configuration of a probe according to an exemplary embodiment.

FIG. 20 is a block diagram of a configuration of a probe 20A according to another exemplary embodiment.

Referring to FIG. 20, the probe 20A according to the present exemplary embodiment may include a transducer array 21, an ultrasound transceiver 22, an image processor 23, and a communicator 24. The transducer array 21, the ultrasound transceiver 22, and the image processor 23 may have substantially the same configuration as that of their counterparts described above. The ultrasound transceiver 22 and the image processor 23 may be embodied in the probe 20A instead of an ultrasound diagnostic apparatus, in comparison to the probe 20. Thus, the speed of signal processing may be further increased.

The communicator 24 may transmit an echo signal or an output of the image processor 23 to another electronic device. Examples of the other electronic device may include electronic devices such as ultrasound diagnostic apparatuses 1000A, 1000B, 1000C, 1000D, a server, a PC, a mobile phone, and a tablet PC. The communicator 24 communicates with another electronic device by wire or wirelessly. For example, the communicator 24 may include at least one of a close-distance communicator, a wired communicator, and a mobile communicator.

Figure 21:
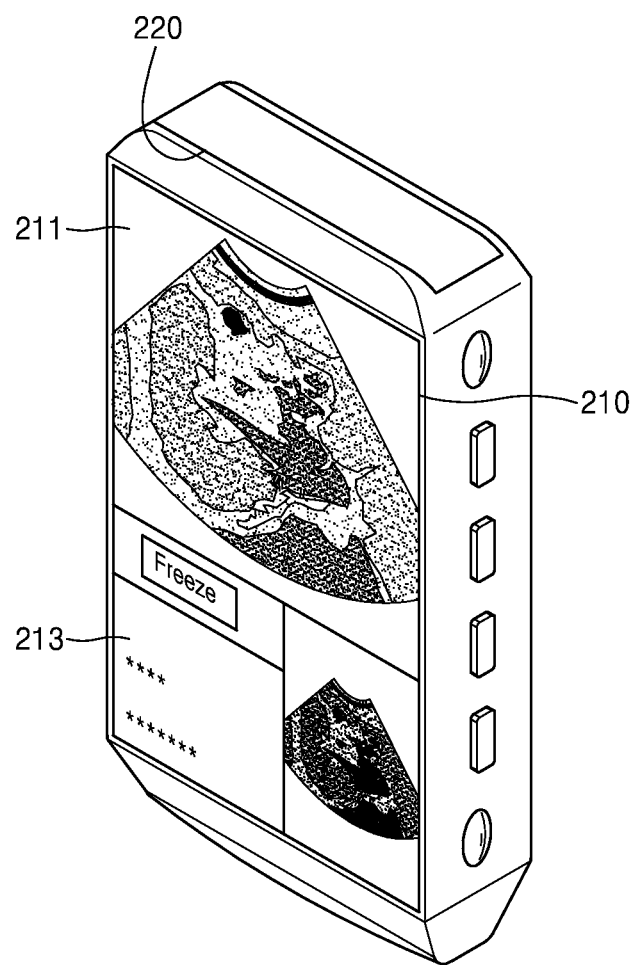
FIG. 21 illustrates a wireless probe according to an exemplary embodiment.

FIG. 21 illustrates a wireless probe 20B according to an exemplary embodiment.

Referring to FIG. 21, the wireless probe 20B according to the present exemplary embodiment may include a screen 210 displayed on a display panel of the wireless probe 20B, and a transducer 220. The screen 210 may include an ultrasound image 211 showing the scanned target object obtained by the transducer 220 and/or a user interface screen 213. The wireless probe 20B may be connected to a medical device via a wireless network and may transmit data to the medical device.

In the present embodiment, the wireless probe 20B may have the configuration of the probe 20A illustrated in FIG. 20. In this case, the transducer array 21, the ultrasound transceiver 22, the image processor 23 and the communicator 24 may be embodied in the wireless probe 20B.

Figure 22:
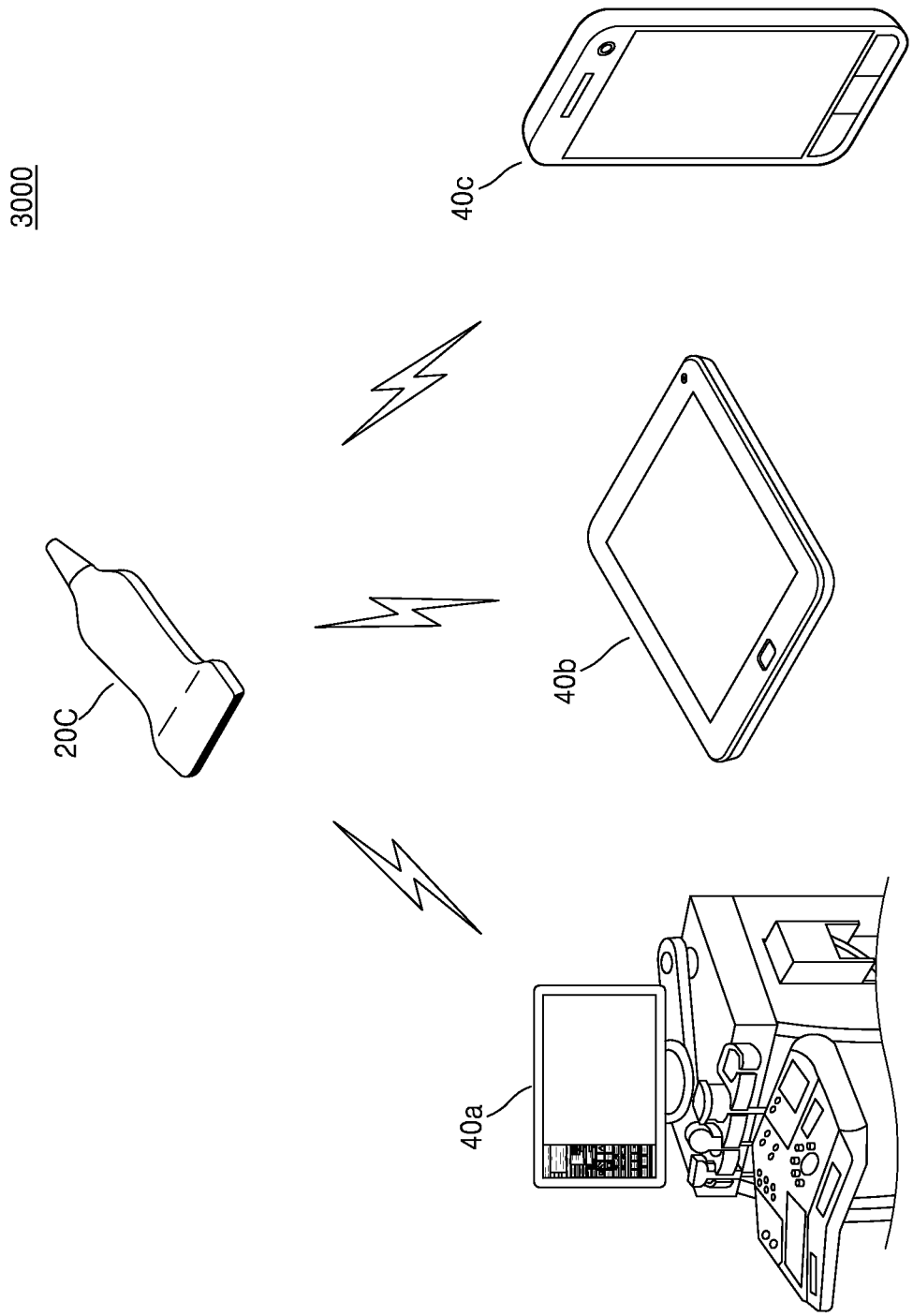
FIG. 22 illustrates a ultrasound diagnostic system having a wireless probe according to an exemplary embodiment.

FIG. 22 illustrates an ultrasound diagnostic system 3000 having a wireless probe 20C according to an exemplary embodiment.

Referring to FIG. 22, the ultrasound diagnostic system 3000 may include the wireless probe 20C. The wireless probe 20C may be connected to a main body 40a, a tablet PC 40b and/or a mobile phone 40c via wireless network. The main body 40a may be implemented as a cart-type main body or a mobile main body. Examples of the main body 40a are a cart-type ultrasound system, a picture archiving and communication system (PACS) viewer, a laptop computer, a personal digital assistant (PDA), or the like, but are not limited thereto.

Figure 23:
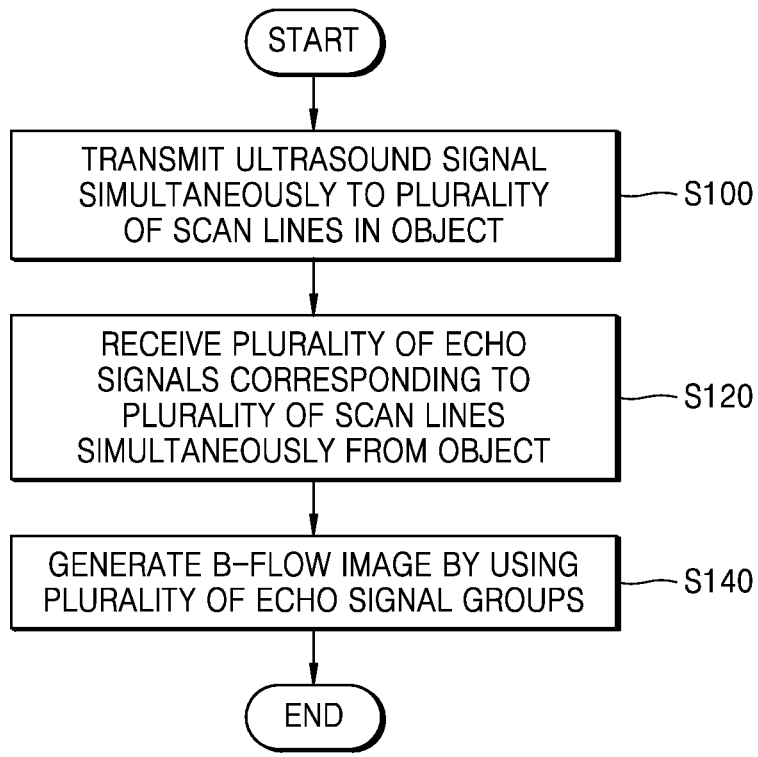
FIG. 23 is a flowchart of a method of generating an ultrasound image according to an exemplary embodiment.

In the present embodiment, the wireless probe 20C may have the configuration of the probe 20A illustrated in FIG. 20. The wireless probe 20C may obtain ultrasound data by transmitting ultrasound signals to a target object and receiving echo signals reflected from the target object. An ultrasound image may be generated by using the obtained ultrasound data, and the generated ultrasound image may be transmitted to the main body 40a, the tablet PC 40c and/or the mobile phone 40c. In this case, the generated ultrasound image may be displayed on the main body 40a, the tablet PC 40c and/or the mobile phone 40c. Alternatively, the wireless probe 20C may transmit the obtained ultrasound data to the main body 40a, the tablet PC 40c and/or the mobile phone 40c, and the main body 40a, the tablet PC 40c and/or the mobile phone 40c may generate an ultrasound image by using the transmitted ultrasound data. FIG. 23 is a flowchart of a method of generating an ultrasound image according to an exemplary embodiment. Referring to FIG. 23, the method according to the present exemplary embodiment includes operations performed by an ultrasound diagnostic apparatus 1000A, 1000B, 1000C, and/or 1000D, which are described above.

An ultrasound signal is transmitted to a plurality of scan lines in an object (operation S100). In an exemplary embodiment, an ultrasound signal having the form of a plane wave may be transmitted to a region corresponding to a plurality of transducers by applying the same delay time for each of the plurality of transducers. According to another exemplary embodiment, an ultrasound signal having the form of a plane wave may be transmitted to a region corresponding to some of a plurality of transducers, which are arranged adjacent to one another, by applying the same delay time for each of the adjacently arranged some of the plurality of transducers.

In an exemplary embodiment, an ultrasound signal having the form of a plane wave may be transmitted to an object. In another exemplary embodiment, an ultrasound signal having the form of a tilted plane wave may be transmitted to an object. In yet another exemplary embodiment, an ultrasound signal that is focused on a focal point outside a B-flow image within an object may be transmitted to the object. In yet another exemplary embodiment, an ultrasound signal that is focused on a focal point outside an object may be transmitted to the object.

A plurality of echo signals corresponding to the plurality of scan lines are received simultaneously from the object (operation S120). In this case, the simultaneously received echo signals may be clustered into a single echo signal group.

A B-flow image may be generated using a plurality of echo signal groups (operation S140). In detail, a plurality of frames in a B-flow image may be sequentially generated by repeatedly using all or some of the plurality of echo signal groups.

Figure 24:
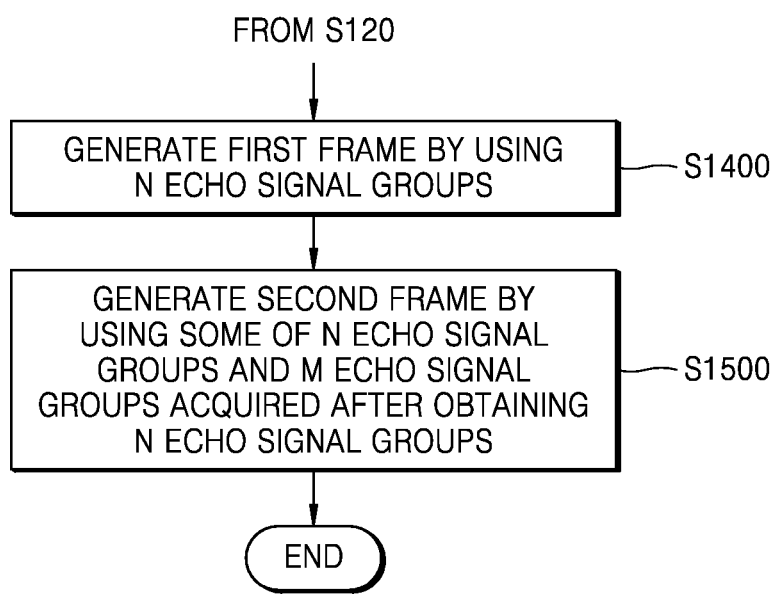
FIG. 24 is a flowchart of an operation of generating a B-flow image, according to an exemplary embodiment.

FIG. 24 is a flowchart of operation S140 of generating a B-flow image in the method of FIG. 23, according to an exemplary embodiment.

Referring to FIG. 24, operation S140 according to the present exemplary embodiment may include operations performed sequentially by the ultrasound diagnostic apparatuses 1000A, 1000B, 1000C, and/or 1000D.

A first frame may be generated using N echo signal groups (operation S1400) wherein N is the number of ensembles corresponding to the number of transmission/reception operations for acquiring a single frame and is a natural number greater than or equal to 2.

A second frame is generated using some of the N echo signal groups and M echo signal groups acquired after obtaining the N echo signal groups (operation S1500). In detail, the second frame may be generated using N−M echo signal groups among the N echo signal groups and the M echo signal groups.

In this case, the N−M echo signal groups may be arbitrarily selected among the N echo signal groups, and M is a natural number less than N.

Figure 25:
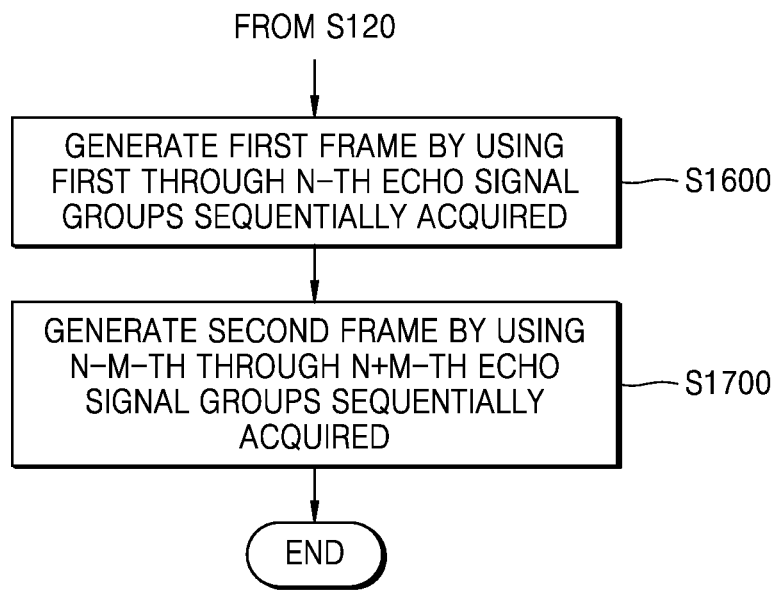
FIG. 25 is a flowchart of an operation of generating a B-flow image, according to an exemplary embodiment.

FIG. 25 is a flowchart of operation S140 of the method of FIG. 23, according to another exemplary embodiment.

Referring to FIG. 25, operation S140 according to the present exemplary embodiment may include operations performed sequentially by the ultrasound diagnostic apparatuses 1000A, 1000B, 1000C, and/or 1000D of FIGS. 3, 4, 18, and 19, respectively.

A first frame is generated using sequentially acquired first through Nth echo signal groups (operation S1600).

A second frame is generated using Nth−M through Nth+M echo signal groups that are sequentially acquired (operation S1700).

Figure 26:
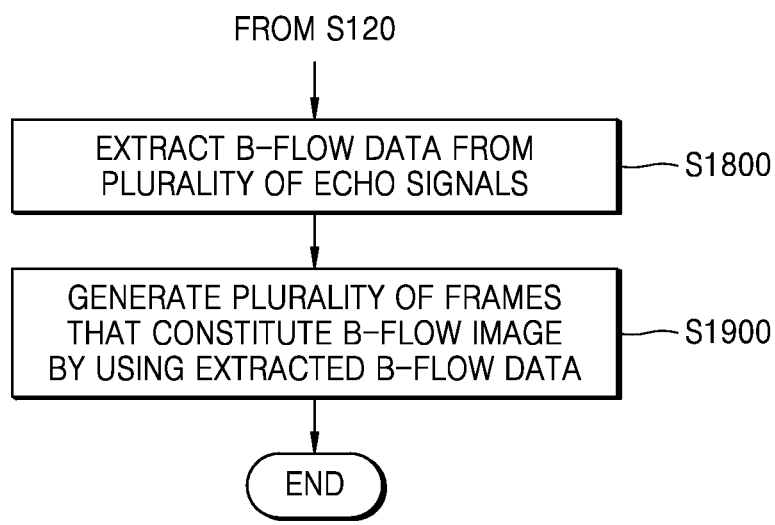
FIG. 26 is a flowchart of an operation of generating a B-flow image, according to an exemplary embodiment.

FIG. 26 is a flowchart of operation S140 of the method of FIG. 23, according to another exemplary embodiment.

Referring to FIG. 26, operation S140 according to the present exemplary embodiment may include operations performed sequentially by the ultrasound diagnostic apparatuses 1000A, 1000B, 1000C, and/or 1000D of FIGS. 3, 4, 18, and 19, respectively.

B-flow data is extracted from a plurality of echo signals (operation S1800).

A plurality of frames that constitute a B-flow image are generated using the extracted B-flow data (operation S1900).

In another exemplary embodiment, operation S140 may further include performing decoding filtering on B-flow data corresponding to a plurality of echo signals for each scan line, which are included in each of a plurality of echo signal groups. In detail, the decoding filtering may be performed by applying a weighted sum to a plurality of echo signals for each scan line, to attenuate a signal corresponding to a tissue component and increase a value of a signal corresponding to a blood flow component.

In another exemplary embodiment, operation S140 may further include performing color mapping on the extracted B-flow data. In this case, in operation S1900, the plurality of frames are generated as a color image.

In another exemplary embodiment, operation S140 may further include extracting B-mode data from a plurality of echo signals and generating a B-mode image by using the extracted B-mode data. In another exemplary embodiment, operation S140 may further include displaying the B-flow image and the B-mode image.

Figure 27:
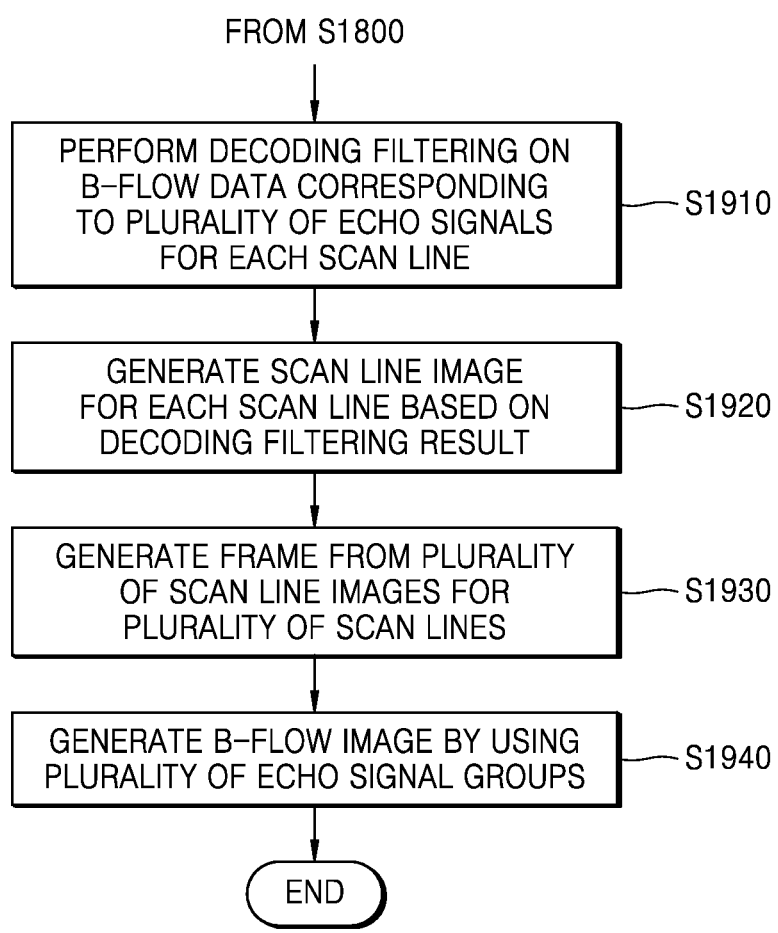
FIG. 27 is a flowchart of an operation of generating a plurality of frames according to an exemplary embodiment.

FIG. 27 is a flowchart of operation S1900 shown in FIG. 26 according to an exemplary embodiment.

Referring to FIG. 27, operation S1900 according to the present exemplary embodiment may include operations performed sequentially by the ultrasound diagnostic apparatuses 1000A, 1000B, 1000C, and/or 1000D of FIGS. 3, 4, 18, and 19, respectively.

Decoding filtering is performed on B-flow data corresponding to the plurality of echo signals for each scan line (operation S1910).

A scan line image is generated for each scan line based on the result of decoding filtering (operation S1920).

A frame is generated from a plurality of scan line images for a plurality of scan lines (operation S1930).

A B-flow image is generated using a plurality of echo signal groups (operation S1940).

Figure 28:
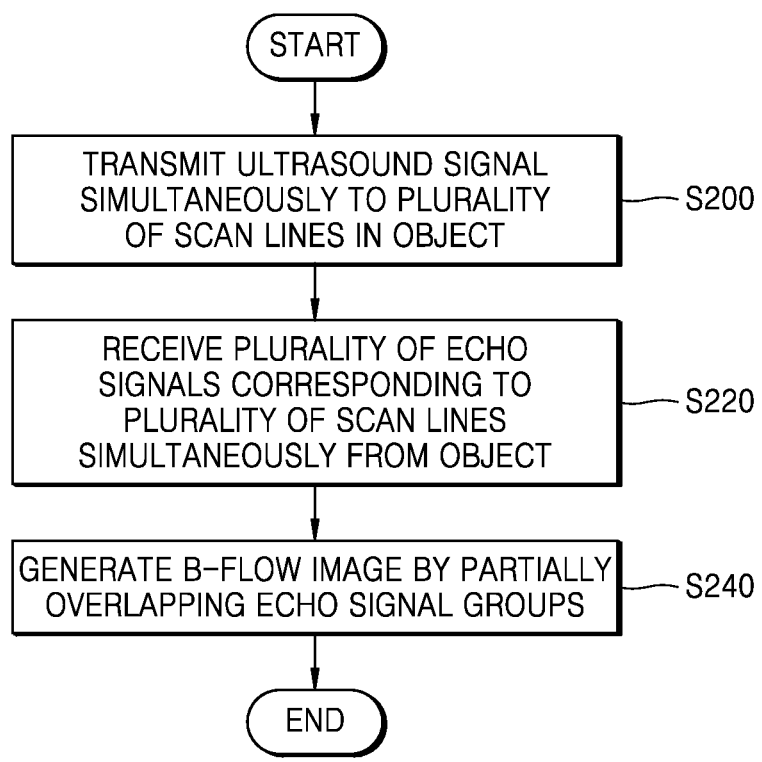
FIG. 28 is a flowchart of a method of generating an ultrasound image according to an exemplary embodiment.

FIG. 28 is a flowchart of a method of generating an ultrasound image according to an exemplary embodiment. Referring to FIG. 28, the method according to the present exemplary embodiment includes operations performed by an ultrasound diagnostic apparatus 1000A, 1000B, 1000C, and/or 1000D, which are described above.

An ultrasound signal is transmitted to a plurality of scan lines in an object (operation S200). In an exemplary embodiment, an ultrasound signal having the form of a plane wave may be transmitted to a region corresponding to a plurality of transducers by applying the same delay time for each of the plurality of transducers. According to another exemplary embodiment, an ultrasound signal having the form of a plane wave may be transmitted to a region corresponding to some of a plurality of transducers, which are arranged adjacent to one another, by applying the same delay time for each of the adjacently arranged some of the plurality of transducers.

In an exemplary embodiment, an ultrasound signal having the form of a plane wave may be transmitted to an object. In another exemplary embodiment, an ultrasound signal having the form of a tilted plane wave may be transmitted to an object. In yet another exemplary embodiment, an ultrasound signal that is focused on a focal point outside a B-flow image within an object may be transmitted to the object. In yet another exemplary embodiment, an ultrasound signal that is focused on a focal point outside an object may be transmitted to the object.

A plurality of echo signals corresponding to the plurality of scan lines are received simultaneously from the object (operation S220). In this case, the simultaneously received echo signals may be clustered into a single echo signal group.

A B-flow image may be generated by partially overlapping a plurality of echo signal groups (operation S240). In detail, a plurality of frames in a B-flow image may be sequentially generated by repeatedly using all or some of the plurality of echo signal groups.

Methods of generating an ultrasound image according to exemplary embodiments may be implemented as a software module or algorithm. Methods implemented as software modules or algorithms may be stored on a computer-readable storage medium as computer-readable codes or program instructions that can be executed on a processor. Examples of computer-readable storage media include magnetic storage media (e.g., Read-Only Memory (ROM), Random Access Memory (RAM), floppy disks, hard disks, etc.) and optical recording media (e.g., CD-ROMs, Digital Versatile Discs (DVDs), etc.). The computer-readable storage media can also be distributed over network-coupled computer systems so that computer-readable codes are stored and executed in a distributed fashion. The computer-readable codes may be read by a computer, stored in a memory, and executed on a processor. When the storage media are connected to the ultrasound diagnostic apparatus 1000A, 1000B, 1000C, or 1000D, the ultrasound diagnostic apparatus 1000A, 1000B, 1000C, or 1000D may be configured to perform methods of generating an ultrasound image according to exemplary embodiments.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of generating an ultrasound image, the method comprising:
 (a) transmitting an ultrasound signal to two or more of scan lines in an object, in a single transmission event;

(b) in response to the single transmission event, receiving, at one receiver channel, two or more echo signals respectively corresponding to the two or more of scan lines;

generating at least three echo signal groups by repeatedly performing steps (a) and (b), each of the at least three echo signal groups being formed to include the two or more echo signals received from the two or more of scan lines as a result of a single execution of each of the steps (a) and (b) with respect to the two or more of scan lines in the object; and generating a B-flow image by partially overlapping the at least three echo signal groups, the B-flow image representing a tissue component and a blood flow component, wherein the generating the at least three echo signal groups further comprises:

generating first echo signal groups comprising ith through Nth echo signal groups, and generating second echo signal groups comprising ith+M through Nth+M echo signal groups using the ith+M through Nth echo signal groups of the first echo signal groups, wherein the generating the B-flow image further comprises:

generating a first frame by using the ith through Nth echo signal groups of the first echo signal groups, and generating a second frame by using the ith+M through Nth+M echo signal groups of the second echo signal groups, wherein i is equal to 1, N is a natural number greater than or equal to 3, and M is a natural number equal to at least 1 and is less than N, and wherein the generating the B-flow image further comprises, extracting B-flow data from the two or more echo signals, performing decoding filtering on the B-flow data extracted from the two or more echo signals for each of the two or more of scan lines, and generating frames that constitute the B-flow image by using the B-flow data on which the decoding filtering has been performed, the first frame and the second frame being included in the frames.

2. The method of claim 1, wherein the transmitting the ultrasound signal further comprises transmitting an ultrasonic plane wave.

3. The method of claim 1, wherein the transmitting the ultrasound signal further comprises transmitting a tilted ultrasonic plane wave.

4. The method of claim 1, wherein the transmitting the ultrasound signal further comprises:

focusing the ultrasound signal on a focal point outside the B-flow image of the object.

5. The method of claim 1, wherein the transmitting the ultrasound signal further comprises:

focusing the ultrasound signal on a focal point outside the object.

6. The method of claim 1, wherein the N is equal to a number of ensembles corresponding to a number of transmission/reception operations for acquiring a single frame among the frames.

7. The method of claim 1, wherein the decoding filtering is performed by applying a weighted sum to the two or more echo signals for each of the two or more of scan lines, to attenuate a signal corresponding to the tissue component and increase a signal corresponding to the blood flow component, among the two or more echo signals.

8. The method of claim 1, wherein the generating the frames further comprises:

generating a scan line image for each of the two or more of scan lines based on a result of the decoding filtering;

generating a frame from scan line images corresponding to each of the two or more of scan lines, respectively; and generating the B-flow image including the frames that are sequentially acquired by repeatedly performing operations of the generating the scan line image and the generating the frame.

9. The method of claim 1, wherein the generating the B-flow image further comprises performing color mapping on the B-flow data, and the generating the frames further comprises generating a color image.

10. The method of claim 1, further comprising:

extracting B-mode data from the two or more echo signals; and generating a B-mode image by using the B-mode data.

11. The method of claim 10, further comprising displaying the B-flow image and the B-mode image.

12. The method of claim 1, wherein the transmitting the ultrasound signal further comprises transmitting an ultrasonic plane wave to a region corresponding to a plurality of transducers by applying a same delay time for the plurality of transducers.

13. The method of claim 1, wherein the transmitting the ultrasound signal further comprises transmitting an ultrasonic plane wave to a region corresponding to some of a plurality of transducers, which are arranged adjacent to one another, by applying a same delay time for the some of the plurality of transducers which are adjacently arranged.

14. An ultrasound diagnostic apparatus comprising:

a transceiver comprising:

a transmitter configured to transmit an ultrasound signal to two or more of scan lines in an object in a single transmission event, and a receiver configured to, in response to the single transmission event, receive, at one receiver channel, two or more echo signals respectively corresponding to the two or more of scan lines, wherein the transmitter is further configured to repeatedly perform a transmission of the ultrasound signal to the two or more of scan lines in the object and the receiver is further configured to repeatedly perform a reception of the two or more echo signals respectively corresponding to the two or more of scan lines, the two or more echo signals forming at least three echo signal groups, each of the at least three echo signal groups being formed to include the two or more echo signals received as a result of a single execution of the transmission of the ultrasound signal and the reception of the two or more echo signals with respect to the two or more of scan lines in the object; and an image processor configured to generate a B-flow image by partially overlapping the at least three echo signal groups, the B-flow image representing a tissue component and a blood flow component, wherein the at least three echo signal groups comprises first echo signal groups comprising ith through Nth echo signal groups and second echo signal groups comprising ith+M through Nth+M echo signal groups, the second echo signal groups are generated by using the ith+M through Nth echo signal groups of the first echo signal groups, wherein the image processor is further configured to generate a first frame by using the ith through Nth echo signal groups of the first echo signal groups, and generate a second frame by using the ith+M through Nth+M echo signal groups of the second echo signal groups, wherein i is equal to 1, N is a natural number greater than or equal to 3, and M is a natural number equal to at least 1 and is less than N, and wherein the image processor is further configured to extract B-flow data from the two or more echo signals, perform decoding filtering on the B-flow data extracted from the two or more echo signals for each of the two or more of scan lines, and generate frames that constitute the B-flow image by using the B-flow data on which the decoding filtering has been performed, the first frame and the second frame being included in the frames.

15. The ultrasound diagnostic apparatus of claim 14, wherein the transmitter is further configured to transmit the ultrasound signal as an ultrasonic plane wave, to the object.

16. The ultrasound diagnostic apparatus of claim 14, wherein the N is equal to a number of ensembles corresponding to a number of transmission/reception operations for acquiring a single frame among the frames.

17. A non-transitory computer-readable recording medium having recorded thereon a program which, when executed by a computer, causes the computer to execute a method of generating an ultrasound image, the method including:

(a) transmitting an ultrasound signal to two or more of scan lines in an object, in a single transmission event;

(b) in response to the single transmission event, receiving, at one receiver channel, two or more echo signals respectively corresponding to the two or more of scan lines;

generating at least three echo signal groups by repeatedly performing steps (a) and (b), each of the at least three echo signal groups being formed to include the two or more echo signals received from the two or more of scan lines as a result of a single execution of each of the steps (a) and (b) with respect to the two or more of scan lines in the object; and generating a B-flow image by partially overlapping the at least three echo signal groups, the B-flow image representing a tissue component and a blood flow component, wherein the generating the at least three echo signal groups further includes:
generating first echo signal groups
comprising ith through Nth echo signal groups, and
generating second echo signal groups comprising ith+M through Nth+M echo signal groups using the ith+M through Nth echo signal groups of the first echo signal groups, wherein the generating the B-flow image further includes:
generating a first frame by using the ith through Nth echo signal groups of the first echo signal groups, and
generating a second frame by using the ith+M through Nth+M echo signal groups of the second echo signal groups, wherein i is equal to 1, N is a natural number greater than or equal to 3, and M is a natural number equal to at least 1 and is less than N, and wherein the generating the B-flow image further includes:
extracting B-flow data from the two or more echo signals,
performing decoding filtering on the B-flow data extracted from the two or more echo signals for each of the two or more of scan lines, and
generating frames that constitute the B-flow image by using the B-flow data it which the decoding filtering has been performed, the first frame and the second frame being included in the frames.

* * * * *